US008249682B2

(12) United States Patent
Cappo et al.

(10) Patent No.: US 8,249,682 B2
(45) Date of Patent: **\*Aug. 21, 2012**

(54) DEVICE FOR MEASURING CONCENTRATIONS OF CONSTITUENTS OF TEAR SAMPLE

(75) Inventors: Anthony P. Cappo, New York, NY (US); Gregory Bennett, New York, NY (US); Jeffrey P Gilbard, Weston, MA (US); Paul T Gavaris, Bethesda, MD (US); Diptabhas Sarkar, Houston, TX (US)

(73) Assignee: Lacrisciences, LLC, Washington, DC (US)

( * ) Notice: Subject to any disclaimer, the term of this patent is extended or adjusted under 35 U.S.C. 154(b) by 1359 days.

This patent is subject to a terminal disclaimer.

(21) Appl. No.: 11/899,596

(22) Filed: Sep. 6, 2007

(65) Prior Publication Data

US 2009/0005660 A1      Jan. 1, 2009

Related U.S. Application Data

(63) Continuation-in-part of application No. 11/030,839, filed on Jan. 7, 2005, now Pat. No. 7,395,103.

(51) Int. Cl.
*A61B 5/1455* (2006.01)

(52) U.S. Cl. ........................ 600/310; 600/318

(58) Field of Classification Search .............. 600/310, 600/318, 584; 356/445; 436/164; 422/82.05
See application file for complete search history.

(56) References Cited

U.S. PATENT DOCUMENTS

| 4,951,683 A | 8/1990 | Davis |
| 4,996,993 A | 3/1991 | York |
| 5,313,264 A | 5/1994 | Ivarsson et al. |
| 5,351,127 A | 9/1994 | King et al. |
| 5,641,640 A | 6/1997 | Hanning |
| 6,594,018 B1 | 7/2003 | Bartholomew |
| 7,017,394 B2 | 3/2006 | Sullivan |

OTHER PUBLICATIONS

Craig, JP et al., "Refractive Index and Osmolaity of Human Tears," Optometry and Vision Science, vol. 72 No. 10 pp. 718-724, 1995.
Ho, H.P., et al., "Application of differential phase measurement technique to surface plasmon resonance sensors," Sensors and Actuators B, vol. 96, pp. 554-559, 2003.

*Primary Examiner* — Eric Winakur
(74) *Attorney, Agent, or Firm* — R. Neil Sudol; Henry D. Coleman; William J. Sapone

(57) ABSTRACT

A medical diagnostic method utilizes a surface plasmon resonance apparatus provided with a sensing surface. A tear sample from an eye of a patient is placed into contact with the sensing surface. The surface plasmon resonance apparatus is then operated to determine concentrations of solutes such as salt and antigenic analytes in the tear sample.

35 Claims, 17 Drawing Sheets

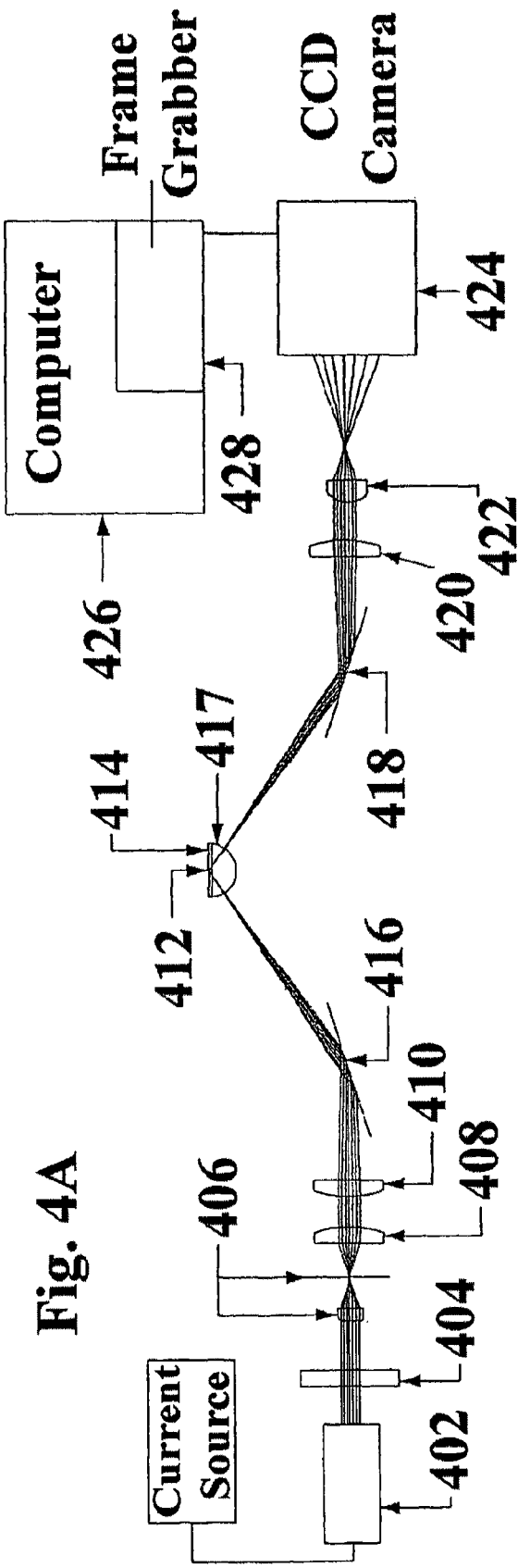
Fig. 4A
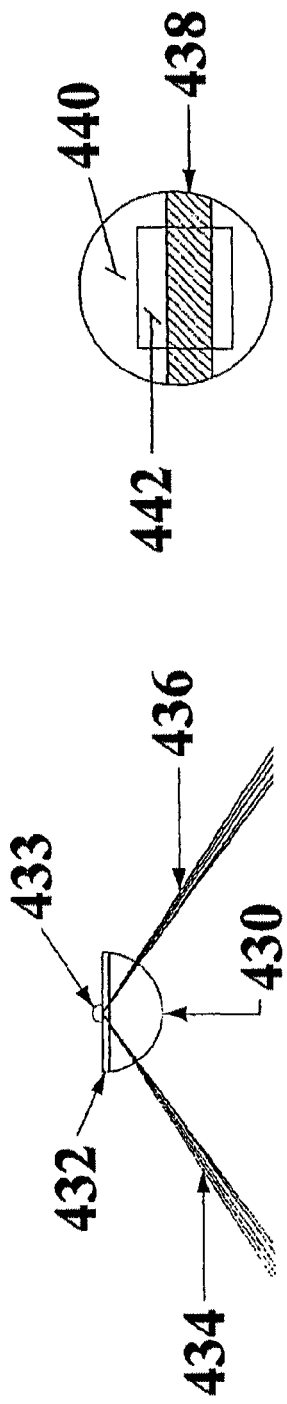
Fig. 4C
Fig. 4B

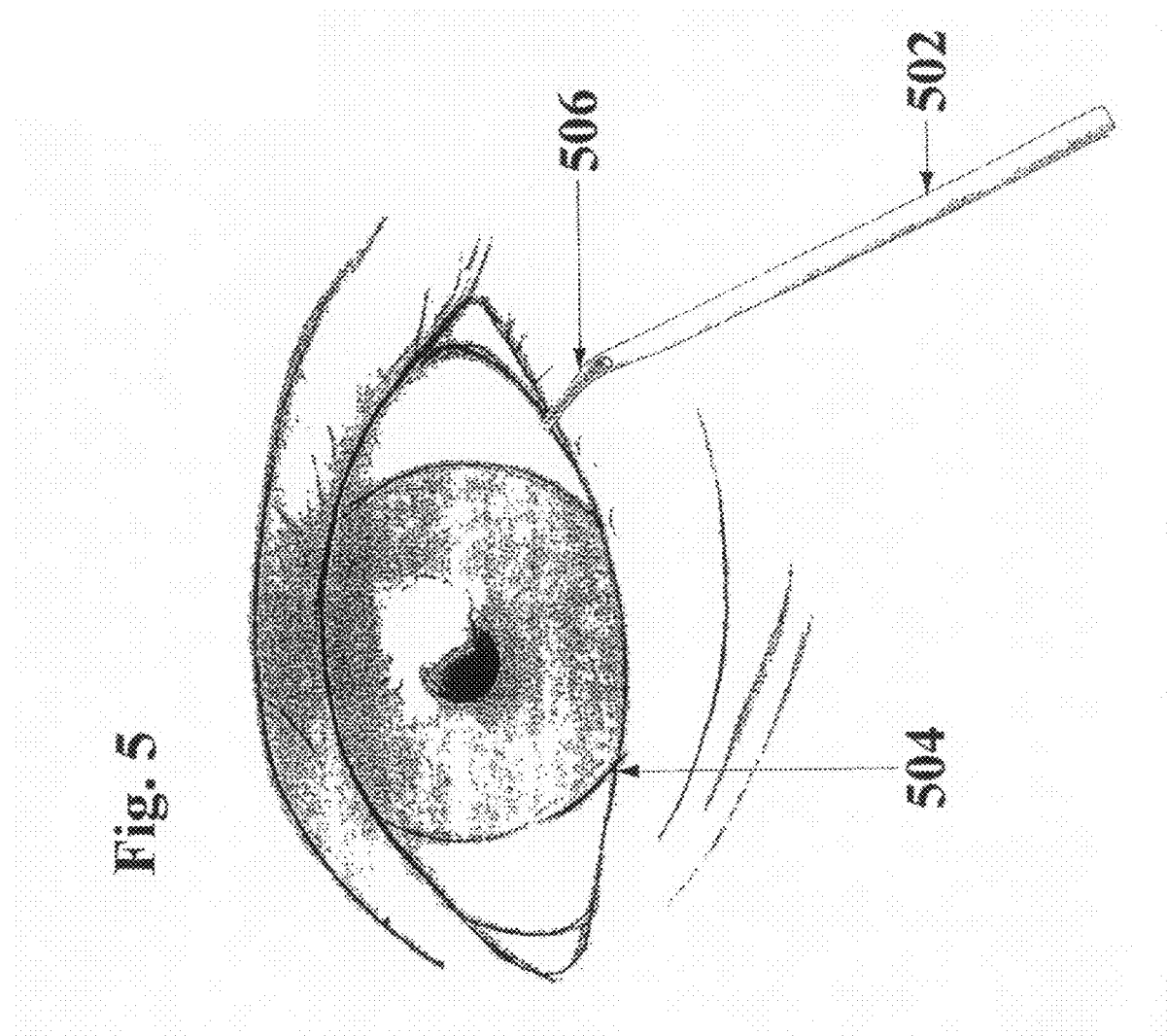

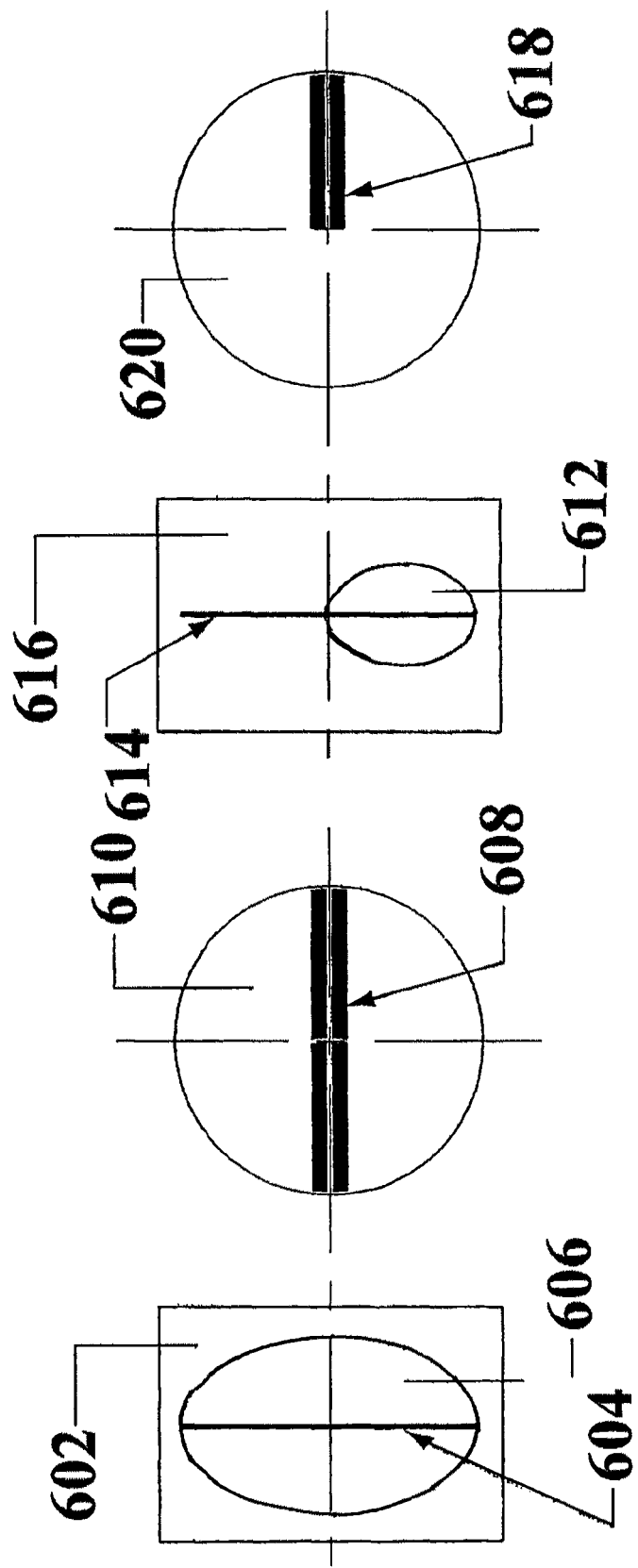

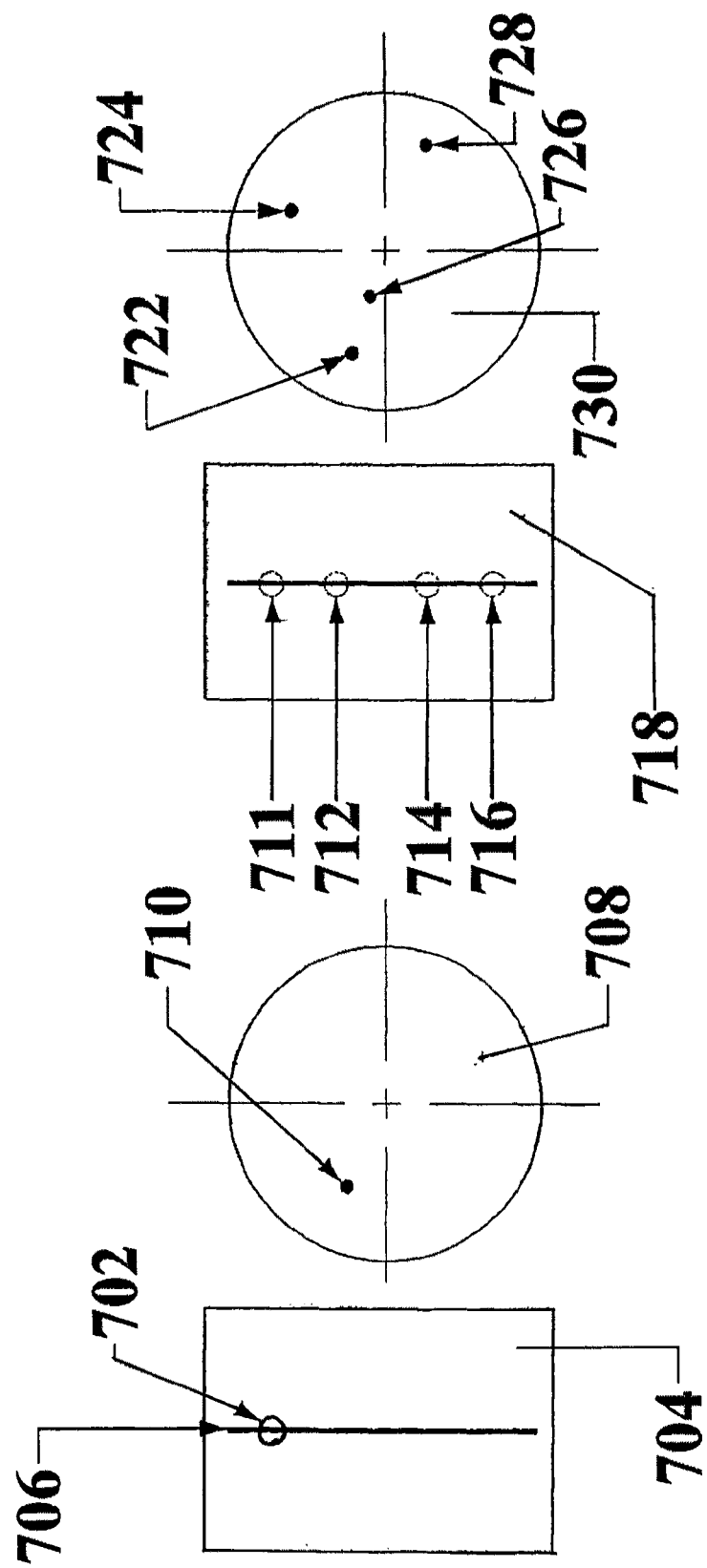

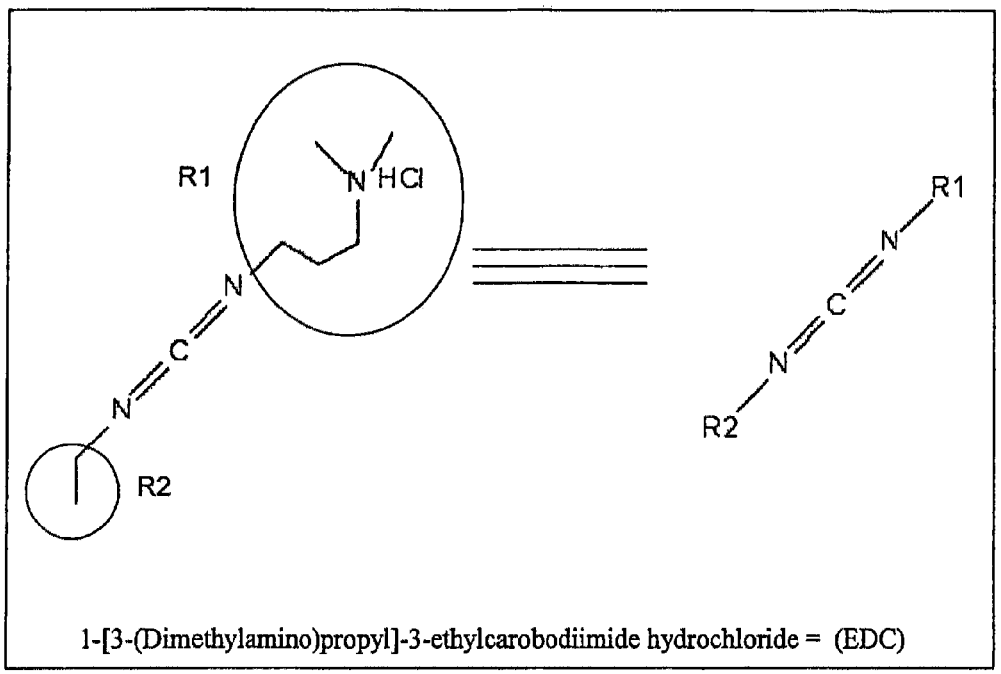
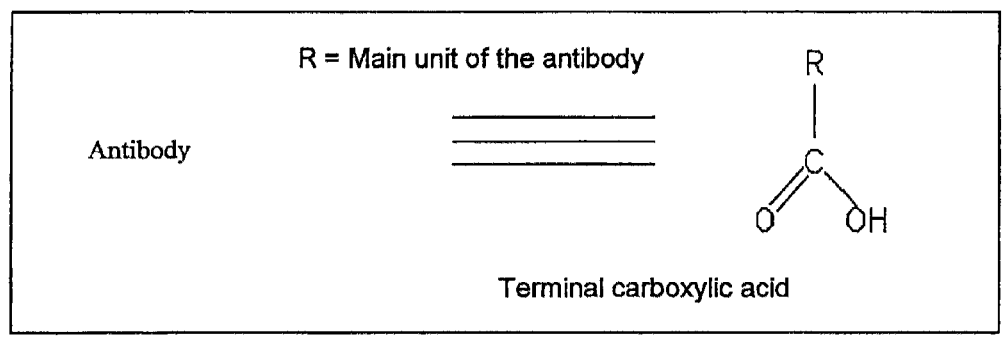
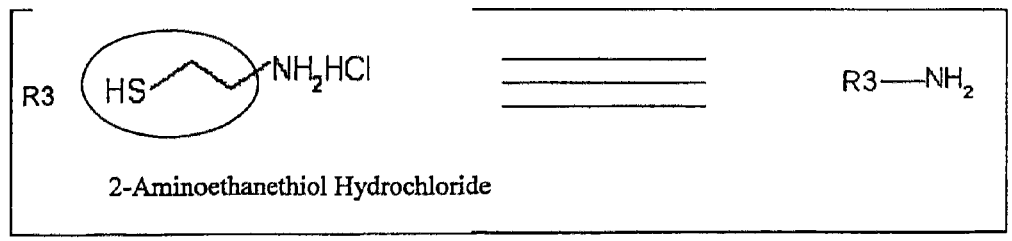
Fig. 16

DEVICE FOR MEASURING CONCENTRATIONS OF CONSTITUENTS OF TEAR SAMPLE

CROSS-REFERENCE TO RELATED APPLICATION

This application is a continuation-in-part of application Ser. No. 11/030,839 filed Jan. 7, 2005.

STATEMENT REGARDING FEDERALLY SPONSORED RESEARCH

This invention and/or unerlying inventions were made with Government support under Grant No. R41 EY01559-01 of the National Institutes of Health's National Eye Institute, Small Business Technology Transfer Program. The Government has certain rights in the invention.

FIELD OF THE INVENTION

This invention relates to an apparatus for measuring selected constituents of tears. The apparatus is useful in the diagnosis of various eye diseases.

BACKGROUND OF THE INVENTION

Dry Eye Syndrome, or Keratoconjunctivitis Sicca (KCS) is one of the most frequently established diagnoses in ophthalmology. Current estimates hold that roughly 40-60 million people in the United States exhibit dry eye symptoms. The lack of accurate statistical data about the occurrence of dry eye is due largely to a lack of state-of-the-art diagnostic equipment. A more disturbing trend, however, is the misdiagnosis of dry eye or its escape from early detection altogether, since symptomatic patients are not always easily identified.

Pursuing more effective diagnosis will strengthen the paradigm of ophthalmic care available in this country. The pharmaceutical industry recognizes this. The first prescription pharmaceuticals for treating dry eye are now appearing on the market, with more on the way in the next twenty-four months, and yet the methods for diagnosis and monitoring treatment remain problematic.

There is no 'gold standard' test that both diagnoses dry eye and monitors the effect of its treatment. The popular method is a matrix of subjective observation of symptoms and objective tests (such as Schirmer testing, staining techniques and tear break-up time) none of which is specific to the detection of dry eye or the measurement of its severity.

Considering recent pharmaceutical advancements aimed at treating dry eye, timely and parallel advancements in diagnostic technologies are needed.

The osmolarity of a tear—the degree of dissolved solids therein—is popularly accepted by experts in the field as an indicator of the presence and severity of dry eye. The instrument most commonly associated with the measurement of tear osmolarity is the osmometer; however, technical limitations have restricted the use of tear osmometers to primarily research environments.

An osmometer is a device that measures the concentration of dissolved solutes in water. Though it is widely used in other fields, osmometers are used in medicine in applications such as determining osmol gap in toxicology and trauma cases, monitoring mannitol treatment infusions, monitoring the absorption in Glycine ingestion with irrigation fluids in surgical procedures, among others.

Despite the suitability of this technology for measuring tear osmolarity, the current devices present certain limitations that prevent their widespread use in a clinical environment. The most prevalent problem has to do with sample size.

Nearly all commercially available osmometers are designed (and perhaps technologically limited) to measure milliliter-size samples. Tear samples extracted from patients tend to be in the nanoliter volumes and further complicating matters, dry eye patients generally have less tears and make handling samples even more difficult. The only osmometer designed to measure nanoliter sample sizes, is no longer available commercially and is too cumbersome for practical use in a clinical environment. The result is that practicing ophthalmologists are left with a haphazard methodology and inadequate tools to accurately detect this prevalent condition.

Dry Eye Syndrome

Dry Eye Syndrome is a complex group of diseases characterized by a decreased production of one or more of the three components of the tear film: the lipid layer, the aqueous layer, and the mucin layer. A deficiency in one of the tear film components may lead to loss of the tear film stability. Normal sight relies on a moist ocular surface and requires a sufficient quality of tears, normal composition of the tear film, regular blinking and normal lid closure as prerequisites. If left untreated, dry eye syndrome can cause progressive pathological changes in the conjunctival and corneal epithelium, discomfort, corneal ulceration's and even ultimately lead to blindness.

Standard treatment has been tear replacement therapy, which attempts to either mimic the human tear film or present a more sophisticated hypo-osmolar version of the tear film. Unfortunately, as dry eye syndrome progresses beyond the mild stage, this common therapy becomes less effective. Further, these treatments do not address the etiology of dry eye.

The precise mechanisms that give rise to dry eye are currently unknown and have been under many debates over the years. Several different mechanisms have been proposed as a possible etiology of dry eye over the recent years, with a general ideology that it is usually caused by a problem with the quality of the tear film that lubricates the ocular surface. More recent research has proposed that dry eye may be a result of a decrease in hormonal status with aging (being more prominent in postmenopausal women), or have an immune basis and acquired inflammatory condition of the ocular surface. Other causes of dry eye symptoms can occur from certain medications (i.e. antihistamines, beta-blockers), associations with certain systemic inflammatory diseases (i.e. rheumatoid arthritis), mechanical causes (i.e. incomplete closure of eyelids), infectious causes (i.e. viral infections) and certain neurological causes (i.e. LASIK procedures). Despite the recent gains in knowledge of possible pathogenic factors of dry eye, there has been a lack of consensus as to the appropriate diagnostic criteria, the specific aims of objective diagnostic testing, the role subjective symptom's play in diagnosis and the interpretation of results.

The symptoms of dry eye vary considerably from one individual to another. Most patients complain of a foreign body sensation, burning and general ocular discomfort. The discomfort is typically described as a scratchy, dry, sore, gritty, smarting or burning feeling. Discomfort is the hallmark of dry eye because the cornea is richly supplied with sensory nerve fibers.

Despite its high prevalence, dry eye is not always easy to diagnose. The vast majority of patients have symptoms that are mild to moderate in severity. Although these patients are genuinely suffering discomfort, objective signs of dry eye may be missed, and without proper diagnosis, patients may not receive the attention and treatment that this condition warrants. The signs and symptoms of dry eye can be misinterpreted as evidence of other conditions such as infectious, allergic, or irritative conjunctivitis. Given these complications in diagnosis, it is estimated that diagnosis rate of dry eye is 20%.

Several drug companies and research sites are formulating drugs to combat and relieve the symptoms of dry eye, many in FDA Phase III trials of their version of treatment. At the date of this writing, the first prescription product for treatment of dry eye is available on the market, followed by others slated for release in as early as 2004 and two others in 2005 and 2006. With no easy way to objectively measure the occurrence of dry eye, the physicians will be left to subjective dispensing of the drug, or either late or misdiagnosis.

Current Objective Diagnostic Methods

Diagnosis of dry eye typically begins with clinical examination. A Schrimer test is usually performed where standardized strips of filter paper are placed at the junction between the middle and lateral third of the lower lid. If after 5 minutes less than 5 millimeters has been wetted there is reason to believe aqueous tear-deficient is present. Though the test is quick, inexpensive and results are available immediately, it provides only a rough estimate and is unreliable in moderate dry eye.

Dye staining is another method of diagnosing dry eye, with either fluoriscein or Rose Bengal, and a trained physician can look for patterns under slit lamp observation indicating dryness. Another test, tear break-up time, is a measure of the stability of the tear film. A normal tear film begins to break up after approximately 10 seconds, and accelerated with patients with dry eye.

The osmometer generally used in measuring tear osmolarity is the Clifton Direct Reading Nanoliter Osmometer (Clifton Technical Physics, Hartford, N.Y.) developed in the 1960's. Although not necessarily originally intended for use in measuring tears, it is one of the few instruments capable of measuring nanoliter volumes of solution and has found its way into ophthalmology.

The Clifton Osmometer was produced in limited quantities over the years, and is not routinely used outside a research laboratory. It is based on the well-known measurement technique called freezing point depression. The Clifton Osmometer measures the osmolarity by measuring the freezing point depression of the tears. In freezing point depression measurements, water which normally freezes at 0° C., in presence of dissolved solutes there occurs a depression in its freezing temperature, the mathematical relationship of which is defined by Raoult's Law.

Though the test can be accurate it requires a very skilled operator to make the measurement. The test monitors the 'depression' by optically examining a fractional volume of a teardrop under a microscope. Due to its limitations and lack of availability, there appears to be only a few units left in the field. Furthermore each measurement can take over fifteen minutes, which coupled with the small sample volumes make the use of Clifton Osmometer an extremely tedious and inconvenient process. The amount of time required and the operating skill demanded are unacceptable to a busy practice or clinic, even if the units were available.

What is direly needed in the hands of a physician performing routine examinations is a simple but accurate device that can screen, track, and help administer treatment and medications at an early stage.

It would also be beneficial to facilitate early detection of other diseases of the eye, and to differentiate between different types of dry eye such dry eye disease based on increased tear film evaporation versus that based on decreased tear secretion. Dry eye due to lacrimal gland disease results in a decrease in aqueous tear production as well as by a decrease in the secretion of protein by the lacrimal gland. In this disease condition tear osmolarity increases while the concentration of proteins decreases. In contrast, in evaporative dry eye disease commonly caused by large palpebral fissure widths or meibomian gland dysfunction, osmolarity increases and protein concentration also increases. Therefore to distinguish between these two conditions, it is useful to know the concentration of proteins in any given tear sample.

OBJECTS OF THE INVENTION

It is an object of the present invention to provide a device and/or an associated method for facilitating the diagnosis of one or more eye diseases.

It is a more particular object of the invention to provide a device to measure the concentrations of at least two components of a tear sample, such as salt concentration and a protein concentration.

Another object of the present invention is to provide such a device that measures osmolarity of tears for diagnosis of dry eye syndrome.

A more particular object of the invention is to provide such a device that avoids at least some of the problems inherent in conventional osmometers, and in particular when measuring osmolarity of nanoliter size samples.

It is further an object of the invention to provide such a device that can be used clinically—that is simple to use, cost effective for the physician and patient, and accurate, thereby overcoming the problems associated with tear osmometers which are primarily confined to a research setting.

These and other objects of the present invention will be apparent from the drawings and description herein. Although every object of the invention is believed to be attained in at least one embodiment of the invention, there is not necessarily any single embodiment that achieves all of the objects of the invention.

SUMMARY OF THE INVENTION

The present invention in part uses Surface Plasmon Resonance (SPR) technology as a sensing platform to preferentially detect analytes or chemical markers, particularly including antigens, in a tear sample. The general strategy involves immobilizing specific antibodies on the SPR sensor surface, which will lead to a signal generation, specific to their respective chemical markers, e.g., antigens.

This feature of the present invention, the use of antibodies immobilized on the SPR sensing surface to detect analytes or solutes such as antigens in a tear sample, recognizes that known concentrations of antigenic analytes in a tear sample may facilitate diagnosis of eye diseases and conditions. For instance, dry eye due to lacrimal gland disease results in a decrease in aqueous tear production and an increase in tear film osmolarity as well as by a decrease in the secretion of protein by the lacrimal gland. In this disease condition, tear osmolarity increases while the concentration of proteins decreases. In contrast, in evaporative dry eye disease commonly caused by large palpebral fissure widths or meibomian gland dysfunction, osmolarity increases and protein concentration also increases. Therefore to distinguish between these two conditions, it is useful to know the concentration of proteins in any given tear sample.

The present invention recognizes that SPR can measure total protein concentration and has been used as such in many applications for protein analysis. The present invention contemplates use of an SPR tear osmometer to measure concentration of protein in a nanoliter tear sample.

The present invention is directed in part to an apparatus that measures the concentrations of one or more solutes or analytes in nanoliter volumes of solution particularly including human tears.

In a preferred embodiment of the present invention, the apparatus measures concentrations of one or more antigenic solutes or analytes in human tear samples. The apparatus includes a Surface Plasmon Resonance Spectroscope. More particularly, the apparatus includes a light source, typically a laser, lenses, mirrors, prisms, a thin film sensing surface, and an optical detector. The apparatus also includes a computer programmed to analyze raw data and output solute or analyte concentration values of the tested solution.

Surface Plasmon Resonance (SPR) is a phenomenon that occurs when light is incident on a metal dielectric interface at a particular angle, so that the reflected light is extinguished. At the particular angle of incident light, the intensity of the reflected light shows a characteristic curve of diminishing intensity well defined by mathematical equations. The energy of the light that is not reflected, is absorbed by the metallic surface and causing an oscillatory mode (resonance) of the electrons in the metal. The first direct measurement of surface plasmon oscillations was observed in 1959, and they have been extensively studied in the scientific research community throughout the 1970's. Scientists have used the technique for such things as measuring refractive index, properties of metallic thin films, and only in 1982 was it suggested that SPR would be useful as a chemical sensor. Since then, SPR has grown to a versatile technique used in a variety of applications. These include absorbance studies, bio-kinetics and biosensing measurements, bulk liquid measurements, gas detection, refractive index measurements, and thin film characterization. In 1992, SPR systems started to appear on the market commercially as a new measurement tool for molecular scale research. One of the major appeals of SPR systems was the inherent sensitivity of the measurement, and supplemented shortcomings found in other forms of spectroscopic measurements.

The essential components of an SPR measurement system are relatively simple. Consisting mainly of a laser source, simple lenses, a thin-film sensing surface, and a detector, the system can be made compact with little effort. One version of a sensing surface consists of a thin film of gold, 50 nanometers thick, which is deposited on glass by means of evaporated thin film technology. The thin gold coating is in practice, difficult to produce without significant experience or by performing iterations to achieve the exact thickness required for the phenomenon to occur. However, a process is described herein for the production of a proprietary thin film coating that produces a strong SPR signal, is durable and well suited for measuring tear osmolarity.

A medical diagnostic method comprises, in accordance with the present invention, providing a surface plasmon resonance apparatus, providing the surface plasmon resonance apparatus with a sensing surface, placing a tear sample from an eye of a patient into contact with the sensing surface, and operating the surface plasmon resonance apparatus to determine a solute or analyte concentration of the tear sample. Typically, the solutes or analytes are antigenic and are measured with a sensing surface provided with antibodies to the antigenic solute or analyte.

Where the surface plasmon resonance apparatus includes a light-sensing device and a computer or microprocessor operatively linked to the light-sensing device, the operating of the surface plasmon resonance apparatus includes operating the light-sensing device to transmit to the computer an electrical signal encoding a pattern of light absorption by the sensing surface and operating the computer or microprocessor to analyze the image from the light-sensing device.

The operating of the computer or microprocessor preferably includes operating the computer or microprocessor to compare an absorption-line position with prerecorded data correlating absorption-line position with (antigenic) solute or analyte concentration.

In accordance with one embodiment of the invention, the operating of the surface plasmon resonance apparatus includes operating the light-sensing device to transmit to the computer multiple electrical signals per second, wherein each of the electrical signals encodes a pattern of light absorption by the sensing surface, the electrical signals being separated from each other by at least one predetermined time interval. In addition, the computer or microprocessor is operated to analyze the pattern of light absorption encoded in each of the electrical signals.

When measuring tear osmolarity with an SPR device, one analyzes the portion of the SPR signal obtained within the first few milliseconds. For a given sample of tear fluid, which contains both salt solution and proteins, the salt solution comprises small molecules or ions that migrate quickly to the sensing surface. The proteins, being more bulky, take more time to reach and bind to the sensing surface. By making a two-part time-based measurement, one measures both a first signal that reflects the concentration of salt (osmolarity) and a second, larger signal that reflects both salt and protein concentration as the protein binds with the sensing surface. One determines the concentration of protein through simple signal subtraction and analysis (i.e., larger signal less smaller signal is proportional to protein concentration).

The computer analysis of the patterns of light absorption determines, for instance, absorption-line positions or angles of maximum absorption by the sensing surface. Thus, the operating of the surface plasmon resonance apparatus may more specifically include operating the computer or microprocessor to determine a surface resonance angle or absorption-line position from each of the electrical signals.

These resonance angles or absorption-line positions include a first resonance angle or absorption-line position associated with a temporally first one of the electrical signals and a second resonance angle or absorption-line position associated with a later one of the electrical signals. The operating of the surface plasmon resonance apparatus may then further include operating the computer or microprocessor to compare the first resonance angle or absorption-line position to entries in a first calibration table to determine a first solute concentration value, to subtract the first resonance angle or absorption-line position and the second resonance angle or absorption-line position from one another to determine a resultant resonance angle or absorption-line position, and to compare the resultant resonance angle to entries in a second calibration table to determine a second solute concentration.

The surface plasmon resonance apparatus may take the form of a portable probe. In that event, the placing of the tear sample comprises manipulating the probe to bring the sensing surface into contact with a tear-bearing portion of a patient's eye. Moreover, providing the surface plasmon resonance apparatus with the sensing surface may comprise disposing a metallic film carrying sheath in a predetermined position on an operative tip of the probe.

Pursuant to an alternative method of the present invention, the placing of the tear sample comprises extracting the tear sample from a patient's eye and depositing the tear sample on the sensing surface. The tear sample may be extracted and deposited using a micropipette. Alternatively, the tear sample may be extracted and deposited using an absorbent porous material such as blotter paper.

The present invention contemplates that the first solute concentration is a salt concentration. This is because salt migrates more quickly to the sensing surface than the other solute components of a tear sample. Concomitantly, to obtain an absorption-line position or sensing-surface resonance angle that corresponds only to the salt concentration of the tear sample, it is necessary to obtain a measurement before any substantial quantity of the other solutes (e.g., proteins, bacteria) has sufficient opportunity to migrate to the sensing surface. In that situation, the shift of the absorption-line or sensing surface resonance angle relative to a base position (refraction angle determined by the solvent, water, and not by any solute) is due to the salt concentration of the tear sample alone and not to any other solute concentration. Preferably, the first measurement is obtained as soon as the tear sample contacts the sensing surface. However, a delay of no more than about 1/30 second from the time of deposition of the tear sample on the sensing surface is generally sufficiently quick so that the initial video signal captures the salt concentration with little or no error due to concentrations of other substances. Incidentally, where the measurement probe contacts an eye surface to obtain a tear sample, this first signal, as well as several subsequent measurements, are necessarily made while the probe is still in contact with the eye.

A medical diagnostic system comprises, in accordance with the present invention, a surface plasmon resonance apparatus having a sensing surface for contacting a tear sample from an eye of a patient and further having a light-sensing device and a computer or microprocessor operatively linked to the light-sensing device for receiving therefrom an electrical signal encoding a pattern of light absorption by the sensing surface. The computer or microprocessor is programmed to analyze data from the light-sensing device to determine a parameter related to a solute concentration of the tear sample in contact with the sensing surface.

The light-sensing device may be a camera such as a charge-coupled device. In that case, the electrical signal is a video signal. Alternatively, the light-sensing device may be a multi-element photodiode and the electrical signal. Then the electrical signal is an analog difference signal.

The computer or microprocessor preferably includes means for comparing an absorption-line position with prerecorded data correlating absorption-line position with solute concentration.

In one embodiment of the present invention, the plasmon surface resonance apparatus includes a handheld portable casing with an operative tip adapted to facilitate contact of a sensing surface on the operative tip with a tear-bearing portion of a patient's eye.

The sensing surface of a plasmon surface resonance apparatus in accordance with the present invention may include a first layer of a first metal such as gold disposed on a second layer of a second metal such as chromium. Of course, the combinations or signal layers of metals may prove useful.

Where the concentration of a solute other than salt is to be measured, the sensing surface is also provided with antibodies to the particular solute or moiety. The antibodies may be attached to the metals layers of the sensing surface by chemisorption, for instance, mediated by thiol groups of the antibody ligands. And by attaching the relevant antibody, the concentration of any antigen in the tears can be measured.

A feature of the present invention is its ability to measure nanoliter volumes of tears, a typical volume associated with normal and dry eye patients. The apparatus is useful in determining the presence and degree of dry eye syndrome, as osmolarity levels of tears are known to correlate with the severity of dry eye. The measurement of osmolarity is obtained virtually instantaneously once the sample is placed on the sensing surface, and therefore no problems of evaporation are encountered which could introduce errors.

BRIEF DESCRIPTION OF THE DRAWINGS

FIG. 4a is a more detailed optical schematic of an osmometer in accordance with the present invention.

FIG. 4b is an optical diagram showing a more detailed view of the sensing surface, hemicylindrical prism, sample solution, and ray path.

FIG. 4c is a diagram depicting the image on the CCD camera when the beam is allowed to diverge in order to produce a broader line.

FIG. 5 is a schematic perspective view of a patient's eye and a micropipette showing the process of extracting a tear from the patient with the micropipette.

FIG. 6a is a schematic top view of the sensing surface of the osmometer of FIG. 4a with a drop of solution covering the entire laser line image.

FIG. 6b is a representation of the corresponding image seen by the CCD camera.

FIG. 6c is a schematic top view of the sensing surface of the osmometer of FIG. 4a, similar to FIG. 6a, showing a drop of solution covering only half of the laser line image.

FIG. 6d is a representation of the corresponding image seen by the CCD camera.

FIG. 7a is a schematic top view of the sensing surface of the osmometer of FIG. 4a with a nanoliter drop covering the small portion of the laser line image.

FIG. 7b is a representation of the corresponding image seen by the CCD camera.

FIG. 7c is a schematic top view of the sensing surface of the osmometer of FIG. 4a, similar to FIG. 7a, showing four nanoliter drops covering several points along the laser line image.

FIG. 7d is a representation of the corresponding image seen by the CCD camera.

FIG. 16 is a diagram of chemical component used to immobilize an antibody on a gold sensing surface of an SPR osmometer in accordance with the present invention.

DETAILED DESCRIPTION OF THE PREFERRED EMBODIMENTS OF THE INVENTION

The invention will now be described in more detail by way of example with reference to the embodiments shown in accompanying figures. It should be kept in mind that the following described embodiments are presented by way of example only and should not be construed as limiting the inventive concept to any particular physical configuration.

Figure 1:
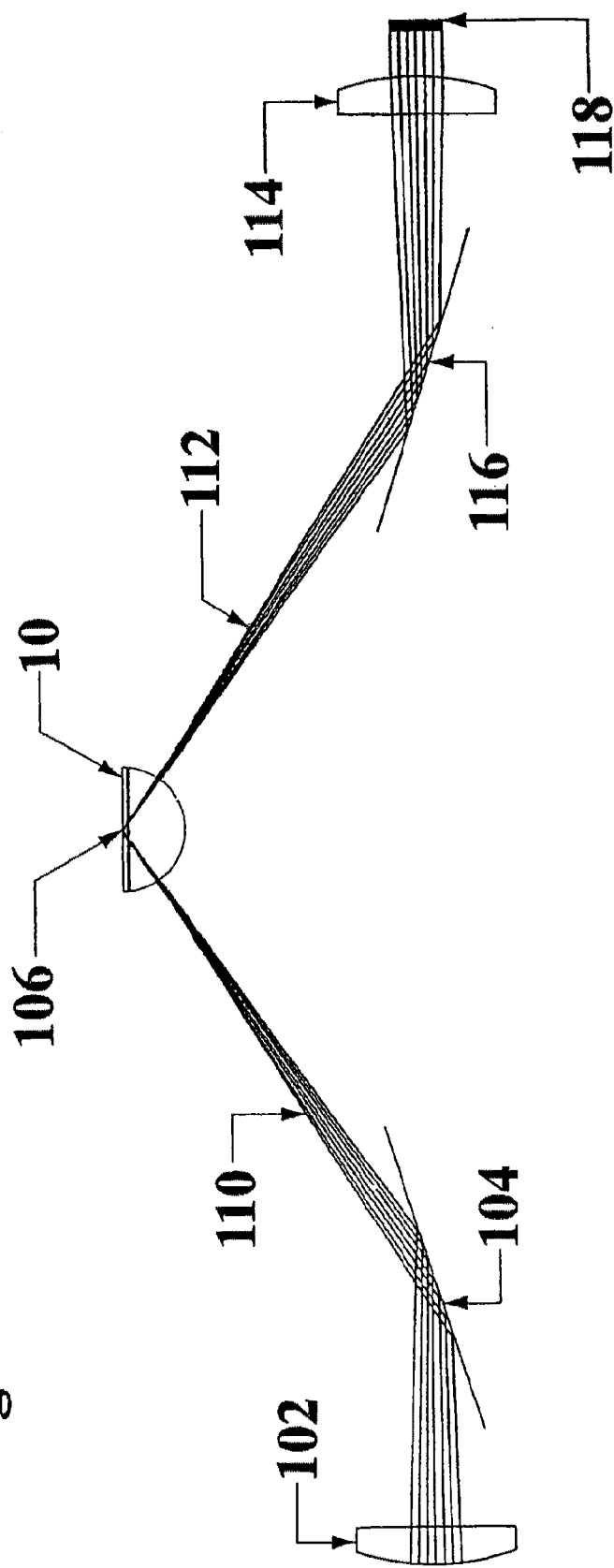
FIG. 1 is an optical schematic in cross section showing the basic components of an osmometer in accordance with the present invention.
Figure 2C:
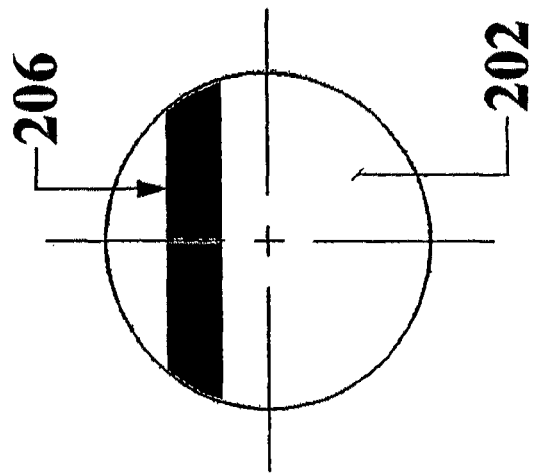
FIG. 2c is a diagram of an image seen by a CCD camera of the osmometer of FIG. 1 when a sample with an increased salt concentration is on the sensing surface.
Figure 2B:
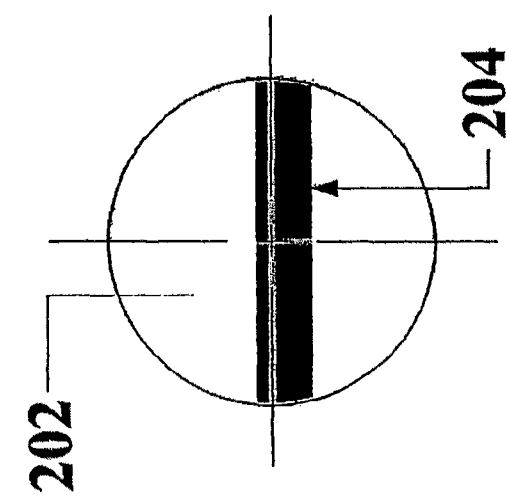
FIG. 2b is a diagram of an image seen by a CCD camera of the osmometer of FIG. 1 when a sample with a particular salt concentration is on the sensing surface.
Figure 2A:
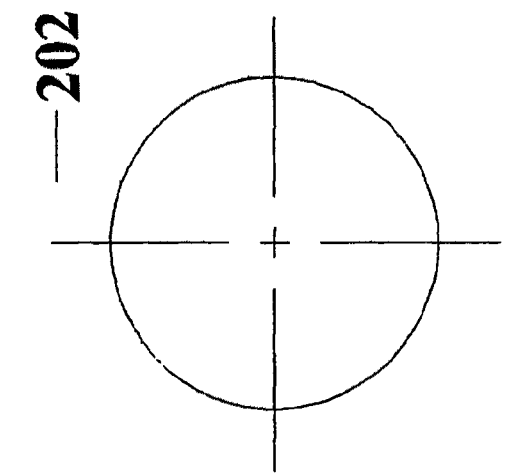
FIG. 2a is a diagram of an image seen by a CCD camera of the osmometer of FIG. 1 when no sample is on a sensing surface.

A preferred embodiment of the present invention is shown in cross section in FIG. 1. In SPR spectroscopy, we are interested at what angle does the incidence light striking the sensing surface diminishes to zero upon reflection. Light from a laser is focused by a cylindrical lens 102 after reflecting from an angled mirror 104 into a line image 106 onto gold-coated sensing surface 108. Since the laser beam is convergent 110, multiple angles of light are incident on the sensing surface at once. The reflected light 112 is then collimated by a second cylinder lens 114 after reflection from an oppositely angled mirror 116 to the first, falls on a charge-coupled device (CCD) camera 118. With no sample on the sensing surface, the resulting image seen by the camera is simply a bright field 202, that is, all pixels on the CCD see the same amount of light as shown in FIG. 2a.

A main object of the invention is to determine the osmolarity of an unknown sample of solution whose volumes are on the order of nanoliters. Osmolarity is essentially the concentration of salt in water and can be expressed in units of milliosmos (mOs). The following description outlines how the apparatus detects changes in osmolarity, with a more detailed description to follow.

Figure 3A:
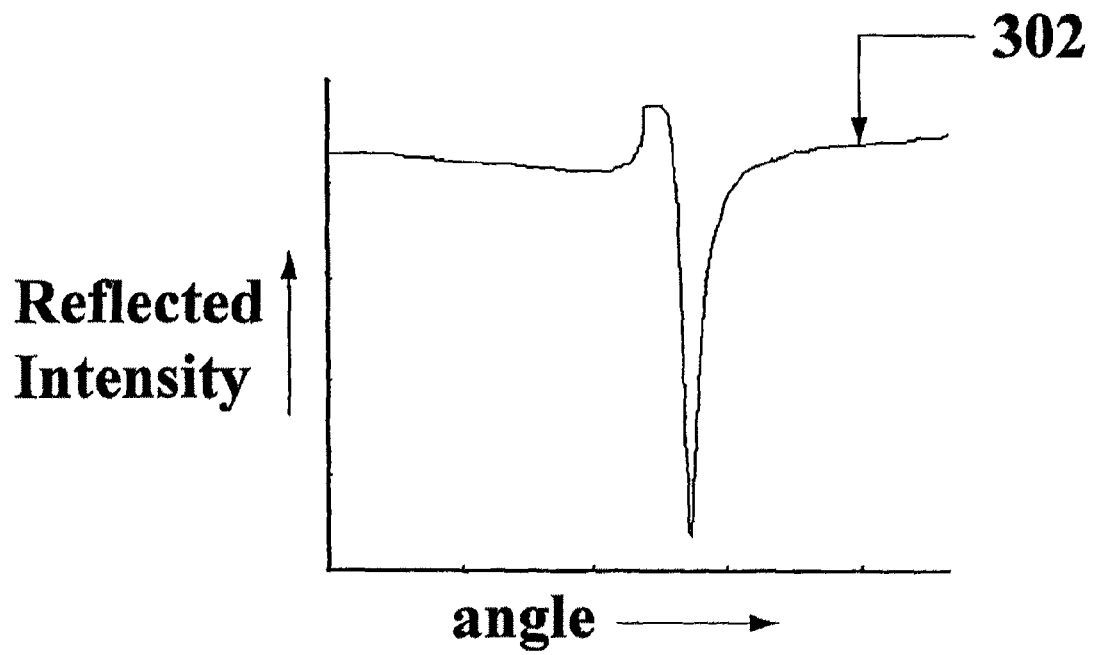
FIG. 3a is a graph showing the characteristic intensity versus angle curve position where surface plasmon resonance occurs when a sample is deposited on the sensing surface of the osmometer of FIG. 1.
Figure 3B:
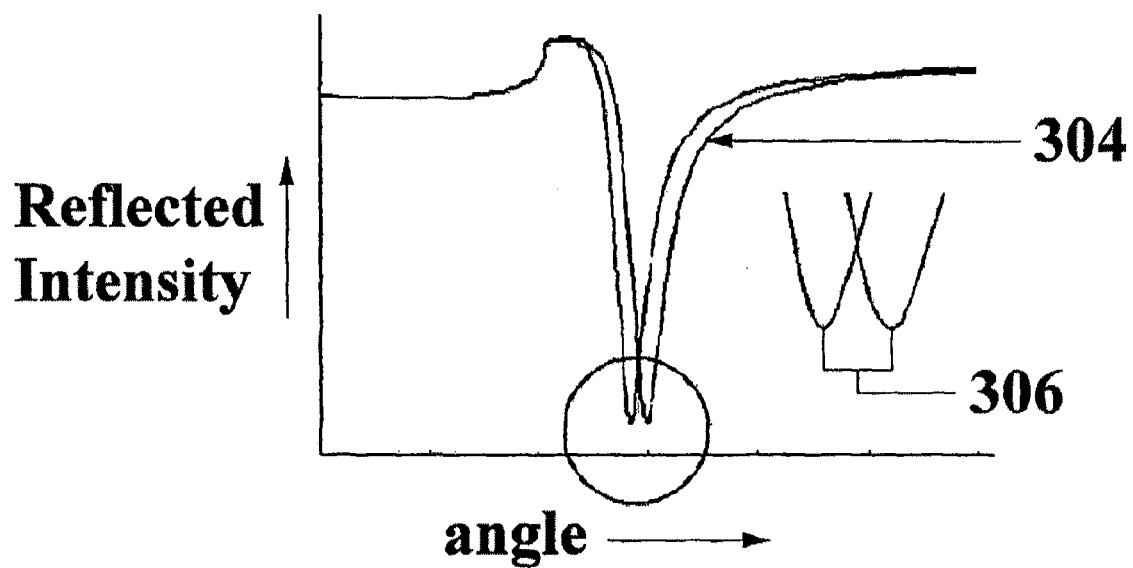
FIG. 3b is a graph showing the result from two different samples placed on the sensing surface of the osmometer of FIG. 1 and the resulting shift in the characteristic curve.

In the particular setup shown in FIG. 1, if a droplet of water is introduced on the sensing surface 108, surface plasmon resonance occurs, and light from one of the angles in the convergent beam 110 is completely absorbed into the gold layer of the sensing surface. The resulting image seen by the camera 118 is the same bright field 202 with a dark horizontal line 204 in the image as shown in FIG. 2b. Now, if a salt crystal (i.e. table salt) is put into the droplet of water on the sensing surface, the dark line in the image 206 will shift upward amongst the bright field 202 as the salt crystal dissolves (FIG. 2c) essentially indicating a change in refractive index. This corresponds to a shift in the angle (delta θ) of light where the surface plasmon resonance occurs—i.e. a different ray in the convergent beam 110. If one were to plot the intensity in the vertical (y) direction across the image shown in FIG. 2b, the characteristic SPR curve 302 will be obtained which is well defined by mathematical equations and is shown in FIG. 3a. Increasing the salt concentration in the water drop on the sensing surface by adding additional salt will force the dark line to move even further vertically. If one were to plot the intensity of the dark line in FIGS. 2b and 2c, a lateral shift in the SPR curve 304 is seen indicative of a change in the angle of where the phenomenon occurs, as shown in FIG. 3b as a delta θ (306) and is directly related to the change in osmolarity. Therefore with calibration, we can determine the exact salt concentration or osmolarity, of an unknown solution.

Practical System Considerations

A more detailed examination of the present invention will now be described. Referring to FIG. 4a, an SPR based nanoliter tear osmometer uses a laser diode module (diode laser plus collimating and circlizing optics) 402 as the light source with a wavelength equal to 670 nm, however any of the various types of laser sources can be used—gas, solid state, semiconductor, etc. For SPR to occur, the laser light must be polarized in a plane parallel to the sensing surface, and therefore a polarization filter 404 is inserted into the laser beam ensuring one plane of polarization. SPR can be observed at virtually any wavelength of light, but will be described here using 670 nm ('red') since the prototype was designed to function at that wavelength.

Following the polarizing filter, a spatial filter (consisting of a short focal length lens and a pinhole) 406 is used to rid the laser beam of any noise. Unfiltered laser beams will contain spatial noise from particles in the air, dust on lenses, etc., and the result will be a beam with unwanted diffraction patterns which can add complexity to image processing during data analysis. The lens and the pinhole in the spatial filter are chosen for the particular laser wavelength to optimize filtering (i.e. 6 mm focal length lens and 10 micron diameter pinhole).

Light exiting the spatial filter is diverging and is collimated with a spherical lens 408. After collimation the light enters a cylindrical lens 410 and the beam is focused to a line image 412. The sensing surface 414 where the tear sample is to be placed needs to be horizontal (in the simplest case)—if it were vertical the tear sample would have a tendency to fall off. Therefore, an angled mirror 416 intercepts the beam before reaching focus and diverts the line image to a horizontally placed sensing surface 414. The reason a cylindrical lens is used (instead of spherical lens) is to produce a focused line image. Given this line image, a sample of tear can be placed anywhere on the line and an SPR signal will be seen; additionally multiple samples can be analyzed at once by placing them along the length of the line image.

The cylindrical lens generates a converging cylindrical wavefront and a focused line image at the sensing surface. For SPR to occur, the laser light must be in a dielectric medium (i.e. glass) and then strike the metallic gold sensing surface. This is usually accomplished by means of an equilateral prism with the gold deposited on the based of the prism. However, the flat faces of the prism will introduce refraction of every ray incident, and to simplify the mathematics, a cylindrical 'prism' 417 is used. This prism is a half of a cylinder made out of optical glass. It can be conveniently fabricated by centerless grinding a rod of a particular glass and then polishing the outer diameter. The rod can then be ground in half along the axis of the cylinder and the flat of the cylinder face is polished producing a 'hemi-cylinder'. By using a cylindrical prism, the surfaces introduce no refraction since all rays entering the prism are perpendicular to the surface. The sensing surface can simply be the polished face of the cylindrical prism and a thin film of gold can be deposited directly on this surface. However, in practice the cylindrical prism was made 1 mm less than a full hemi-cylinder and flat glass plates of the same material with the same dimensions as the flat face of the cylinder were made to 1 mm thick. It is one these glass plates where the gold is deposited making up the sensing surface, since it is simpler to fabricate many of these plates than prisms. The cylindrical prism and glass plate with deposited gold are assembled together with index matching fluid, so to the incoming light the assembly appears as one unit (i.e. there are no changes in media and hence reflections between the cylinder prism and the glass plates). FIG. 4b shows a cylindrical prism 430 and a gold deposited sensing surface 432 assembled with index matching fluid with a sample drop 433 on the sensing surface. Additionally is shows multiple angle light rays entering the prism at 434 and exiting the prism at 436, in each case without refraction.

Deposition of the gold onto the glass plates is a difficult process, since an exact thickness of gold is required for a strong SPR signal. Adding to the complexity, gold when vacuum deposited, does not stick very well to glass, and as such simple cleaning of the surface would wipe away the deposited gold. To make the gold more robust, the well-known technique of first depositing chromium is used. In our system, 2-5 nanometers of chrome is deposited followed by 50 nanometers of gold. It is somewhat difficult in practice to obtain exactly 50 nanometers of gold, and several test runs were performed in order to calibrate the evaporation coating chambers to achieve a usable thickness somewhere between 50 and 55 nanometers of gold. It turns out the amount of chrome used can be critical as well. If too little chrome is used, the gold is not very durable and has a tendency to lift off during handling or use. If too much chrome is used a low SPR signal is seen or even none at all.

Since the wavefront entering the prism is convergent, this means that a range of angles will be incident onto the sensing surface. The SPR minimum occurs at only one particular angle for a given solution. For example, if the media surrounding the sensing surface is air, the angle where SPR will occur (reflected intensity minimum) will be ~33 degrees. If water is introduced as the media on the sensing surface in the form of a drop 433 as shown in FIG. 4b, SPR will occur at ~54 degrees. Since the object of the invention is to measure varying concentrations of salt dissolved in water, and there is a range of human tear osmolarities that determine the presence and degree of dry eye, the apparatus has a range of angles ('dynamic range') that are within the range of SPR occurrence for these solutions. For example, our system has a convergent beam of +/−5 degrees. The range of osmolarity of human tear is roughly 300 mOs to 400 mOs. In an ideal system one would be able to assign a fraction of a degree to say 1 mOs, and determine osmolarity with extreme accuracy. In practice however, the change in angle as osmolarity changes is very small, on the order of 0.1 degree over the range of 300-400 mOs, which introduces challenges in signal detection.

Again referring to FIG. 4a, after the light is allowed to focus to a line image it reflects and diverges from the gold sensing surface. If a sample is in place, the reflected image exhibits a dark line, generally shown in FIG. 3a or b. This exiting light is reflected by a similarly placed mirror 418 at an opposite angle to the first, to bend the light back onto the original optical axis of the laser. A second cylinder lens 420 then collimates this diverging light. A charge-coupled device (CCD) camera 424 can be placed perpendicular to the light beam and a bright field with a dark line is obtained as a video signal for later processing. However, since our change in angle is small, on the order of 0.1 degree, this translates to a vertical shift of the dark line from the extreme values of osmolarity to merely 10 or so microns, about the size of a pixel in the CCD camera. Though it is possible to detect movement of the line to less than a pixel by image processing techniques, movement of the line can be increased optically. Instead, a short focal length lens 422 can be inserted after the cylinder lens 420 into the collimated beam that focuses the beam to a small point and then allowed to diverge. If the CCD camera 424 is then placed after the beam is allowed to diverge, the beam quickly gets large, and the result is a large dark line 438 (covering perhaps ¾ of the active area of the CCD 442) surrounded by a bright field 440, shown in FIG. 4c. In this case, the dark line covers many pixels as does its movement, and small movements can be more easily detected. The image on the CCD is captured with frame grabber 428 mounted in Personal Computer 426.

Measuring Tear Osmolarity Using SPR Spectroscopy

Now that the system intricacies have been adequately described, the following will describe its use as a nanoliter tear osmometer.

There are inherent difficulties in handling nanoliter volumes of samples—the maximum amount of tear fluid usually able to be collected from a patient. Extraction of the sample from the patient is relatively simple, however inserting this sample into an instrument can cause difficulties. In osmometers using freezing-point depression technique, the sample must be frozen allowed to thaw, and the point of complete thawing is related to osmolarity. Concern of evaporation comes into play when samples are small and if it occurs, an incorrect reading of the osmolarity will be obtained. Additionally the nanoliter tear sample must be put into some sort of freezing mechanism (i.e. thermoelectric cooling plate), which is observed microscopically. In short, it has been found to be a very difficult process for freezing-point depression osmometers to obtain reliable data, or a device that is simple to use. Freezing-point depression based osmometers are much better suited at measuring larger (milliliter) size samples.

The interesting fact about SPR is that the phenomenon occurs irrespective of the sample size. As long as the solution is in contact with the sensing surface, and covers the focused (line) laser light, SPR will occur. In the prototype apparatus, the width of the focused laser line was approximately 5 microns, and experimentation has shown that nanoliter sample volumes produce identical SPR signals as milliliter size samples.

Calibration

To measure a tear sample osmolarity, the apparatus is first calibrated by way of laboratory made solutions of known osmolarity. Accurately measuring Sodium Chloride and dissolving in triple distilled water made several solutions with different osmolarity. Each one of these solutions was deposited onto the sensing surface and a dark line forms in the image at the same instant. The signal from the CCD camera which captures the image, is fed into a frame grabber 428 installed in a personal computer 426 and the image is digitized by the frame grabber and stored in the computer (FIG. 4*a*). This process is performed for many solutions and an image for each is obtained.

Now that the computer has several images of a bright field with a dark line, it detects the vertical movement of the dark line from solution to solution. The result is a calibration curve that is stored in the computer for later recall. If now a solution with unknown osmolarity is deposited onto the sensing surface, the computer can find the vertical position of the line, compare it to the calibration solution data, and output the osmolarity of the unknown solution in units of milliosmos.

Flow Cell

To make the process of calibration—the deposition of many solutions with different osmolarity on the sensing surface—simpler, a pump system and a flow cell was constructed. This system consists essentially of a fluid input port, a small holding chamber, and a fluid output port. The unit rests atop the sensing surface and a silicone o-ring makes contact with the sensing surface. The unit is screwed place and compression of the o-ring on top of the sensing surface creates a leak-proof seal. Attached to the input port is tubing, the other end attached to a small pump. The input of the pump draws in the calibration fluid, sends it into the flow cell and passes through the holding chamber and out through the exit port. Once the fluid lands on the sensing surface a dark line appears in the image at some vertical height, and it is recorded by the computer. To measure other solutions, the tubing leading to input of the pump is first inserted into water, to wash the sensing surface, followed by a solution of different osmolarity to the first, and the process is repeated. This gives the computer a full set of data in a short period of time if compared with dropping by hand one solution, recording the image, removing the drop, washing with water, applying the next drop, etc.

Tear Extraction

The extraction of tears from a patient is performed with the use of a glass micropipette. Under slit-lamp observation, the physician places the micropipette 502 near the lower lid and just touching the tear strip 504 so that tear fluid (~200 nanoliters) capilates 506 into the micropipette (see FIG. 5).

The tip of the micropipette is tapered from the 3 mm capillary body down to about 0.5 mm, and is bent at an angle to the body. This is such that during tear extraction the body of the pipette can be angled away from the face and that the process does not stimulate excess tear production which can skew the osmolarity reading.

Now that the tear sample is contained in the micropipette tip, there is some difficulty in getting the tear out and placed exactly. This is routinely done by hand, however in a commercial instrument a more convenient manner is needed. Air pressure must be introduced to overcome the capilating action to force the tear out of the micropipette. This can be done with a squeeze bulb or by simply blowing on the end. The dominant issue with handling nanoliter sample volumes is that they are so small and all forces (i.e. surface tension) near the sample are greater than the mass of the sample, which consequently has a tendency to be pulled to whatever object is closest to it or has the greatest surface tension. When the tear is forced out of the micropipette with gentle air pressure, the tear sample will have a tendency to exit the micropipette and roll up the side of the pipette due to surface tension. However, the tear sample if upon exiting the pipette yet still attached to the end is put in close proximity of another surface (i.e. the sensing surface) the surface tension from the sensing surface pulls the sample onto the surface. This takes a considerable amount of skill and practice. Further complicating matters, the tear sample must lie directly on the focused laser beam on the sensing surface. Therefore, a system is contemplated that pulls the tear sample out of the micropipette and accurately places it on the sensing surface. One method is the use of a microdispensing system that is commercially available. This system uses precise air pressure to force an exact amount of fluid out of a syringe (in this case a micropipette) and this in combination with a micropositioning system that will bring the micropipette tip in close proximity with the sensing surface and will allow for accurate dispensing and placement of the tear sample on the focused laser line image. Other work has been done in the area of using electrical force to dispense a small droplet of fluid.

Figure 15:
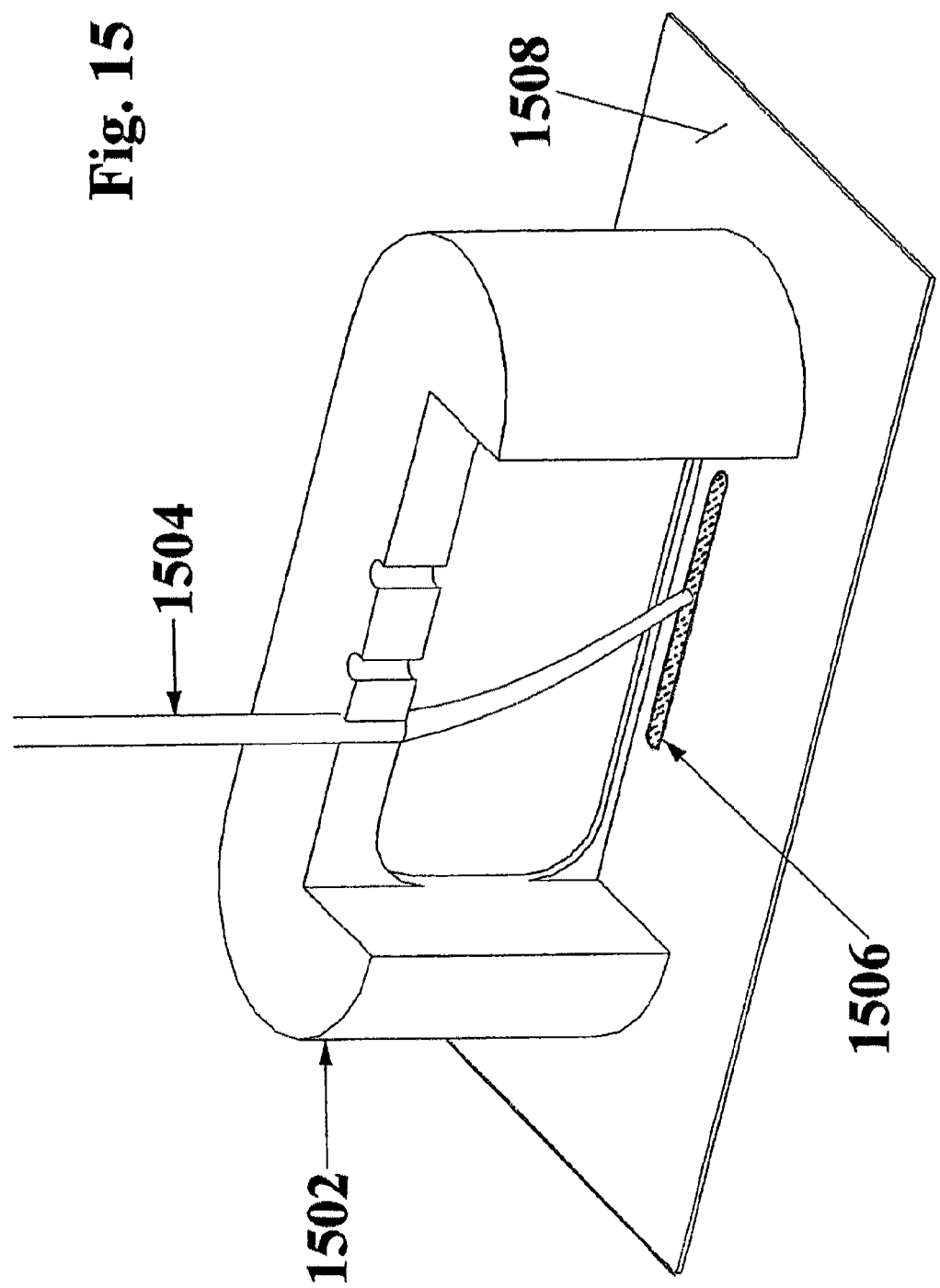
FIG. 15 is a schematic perspective view of a precision micropipette holder that accurately positions a micropipette over the sensing surface of an osmometer in accordance with the present invention.

Placement of the tear on the sensing surface can be simply done with a 3-axis (translation) micropositioning system, which holds the micropipette vertically with the tip facing the sensing surface. Adjustment of the 3 axes via control screws until the tip is right over and nearly in contact with the sensing surface can be done by hand and visual inspection. However, this is inconvenient (and potentially expensive) in a commercial product. The manufacturing of custom micropipettes to a specific tolerance such that the micropipette can be inserted into a fixture mounted over the sensing surface and its position be repeatable is one method for simple accurate positioning of the tear on the sensing surface. FIG. 15 shows a fixture 1502 that was used to position up to three micropipette tips 1504 over and along the focused laser line 1506 on the sensing surface 1508.

One other method for extracting the tear can be done with absorbent material (i.e. paper) that when touched to the tear film or strip absorbs the tear sample. This wet paper then can be touched to the sensing surface and a dark line will appear in the image as before. The advantage to using a paper strip to absorb the tear sample is that a slit lamp microscope is not needed for extraction.

Image Characteristics and Sample Size

Depending on how a solution under test is deposited onto the sensing surface determines the characteristics of the final image. However, all methods will reveal a dark vertical line, surrounded by a bright field. Referring to FIG. 6a, the top view of the rectangular sensing surface is shown at 602. The cylindrical lens in the system focuses laser light to a line image 604 on the sensing surface as shown in the figure. On this sensing surface and covering the line image the sample solution 606 is deposited. The corresponding image is a horizontal dark line 608 in a bright field 610 that translates vertically with change in osmolarity. The length of this line however is determined by the amount of the solution that covers the focused laser line. If the solution 612 only covers half the laser line 614 on the sensing surface 616 as shown in FIG. 6b, the resulting dark line 618 in the image will only cover half of the CCD camera, and the rest will be a bright field 620.

However, when dealing with tears of nanoliter volumes 702, when placed on the sensing surface 704, will only cover a small fraction of the laser line image 706. The result in the image on the CCD will be a bright field 708 with a 'short' dark line 710. This is shown pictorially in FIG. 7a. As the osmolarity of the tear changes, this short line will move vertically in the image. Note that since the sensing surface is large compared to the volume of the tear, it is conceivable that more than one tear (i.e. right eye and left eye) can be placed on the sensing surface at one time, giving immediate readings of both. Additionally, several tears can be placed on the surface at once getting multiple readings. FIG. 7b shows four tear samples 711, 712, 714, 716 with different osmolarity on the sensing surface 718 and the resulting image on the CCD camera showing four dark lines 722, 724, 726, 728 at different vertical positions amongst a bright field 730. The different vertical positions of the lines indicate different osmolarity of each sample.

Image Process Routines for Determination of Vertical Position of Dark Line

As described earlier when a solution is introduced onto the sensing surface the image seen by the CCD camera is shown in FIG. 2a and b. In practice however, this image does just contain a bright field and a dark line, but also noise (bright and dark patches) from spurious reflections and unwanted diffraction from many sources, even with a spatial filter in place. Noise in general can cause an uncertainty in determining the position of the dark line. However, even with this noise, the characteristic SPR signal of diminishing intensity (see FIG. 3) can be seen and with simple averaging a reliable measurement can be made. However, when measuring osmolarity, differences need to be detected on the order of 1 mOs or less, representing a very small change in SPR angle or equally the vertical position of the dark line in the image. Therefore is necessary for the computer to process each image captured from the CCD camera to remove the noise component, or at least reduce it.

The image of the dark line shown in FIG. 2 is not representative of the actual image obtained with the system. In an ideal system with an SPR signal present, if the intensity of the light falling on the CCD camera were plotted vertically along one column of pixels of the CCD the result would be the curve shown in FIG. 3. In reality, this curve has riding on it random noise components. To precisely determine the osmolarity of a solution, the computer must find the minimum of this curve, and compare it to the calibration tables. The more accurately the computer can automatically determine the location of the minimum, the more accurate the measurement of osmolarity will be. With too much noise present, the computer can mistakenly interpret noise as a SPR minimum and report the wrong value of osmolarity. Additionally with noise present, the computer may not be able to detect a small change in movement of the vertical line when solutions close in osmolarity values are measured (i.e. 312.0 mOs and 312.5 mOs). For osmolarity measurements to be useful clinically the system preferably reports osmolarity to within 1-2 mOs of it actual value. Theoretically the system would be able to detect changes down to 0.1 mOs which is likely to be insignificant from a clinical standpoint.

With no sample on the sensing surface the 'baseline' image consists of a bright patch of light. In this bright patch of light contains (spatial) noise. This noise generally consists of diffraction patterns and other patches from interference caused by small scratches or pits in the lens, dust particles, etc. Additionally, the intensity of laser light is Gaussian distributed. All of these unwanted features in the baseline image as present when a sample is placed on the sensing surface and a dark line forms due to SPR. To remove this unwanted spatial noise, the computer can subtract the two images thereby removing these features in the processed image. However, there occurs an amplitude difference between the baseline image and the image with the dark line, so a scaling factor is determined by analyzing the same small portion of each image and comparing the average pixel value between the two areas. The result is a dark field with a bright white line, with the spatial noise component minimized.

There are other sources of noise still present in the signal even after subtraction. These are predominantly random fluctuations such as electronic noise leading to difficulty in determining the exact location (or change in location) of the dark line.

One method is to not only monitor the pixel of minimum intensity representative of the minimum of the dark line, but to monitor it and several pixels around it. The lower portion of the SPR curve containing the point of minimum intensity can be approximated as a parabola. The computer program fits a parabola to the points surrounding the minimum, and then monitors all points on the parabola. In this manner, if the parabola shifts even less than one pixel, the computer can detect it, generally known as subpixel resolution.

Figure 8A:
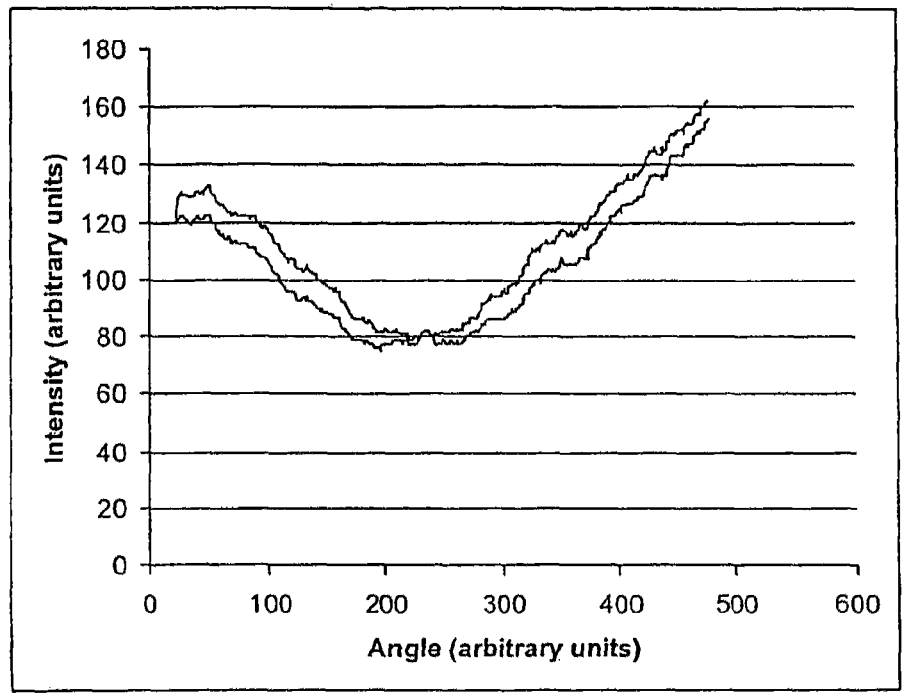
FIG. 8a is a graph depicting the result of placing two different samples on the sensing surface. It shows the intensity of light diminishing and then rising again representing the dark line falling on the CCD. The shift in the two curves represents a change in osmolarity and also shows the noise component present in the prototype system.

If the line is broadened using the diverging lens shown in FIG. 4a it achieves a larger vertical movement of the dark line. If one were to plot the intensity from top to bottom of the CCD, a truncated version of the curve in FIG. 3a will result. If two solutions are tested and the intensity on the CCD is examined at each instant, two broadened truncated curves will be obtained. Actual curves from two solutions tested on the prototype instrument are shown in FIG. 8a. These curves show the diminishing intensity of the laser light reflected from the sensing surface with a sample in place, and contain noise, seen in the figure as high frequency ripples in an otherwise smooth curve. Each curve is shifted slightly to each other indicating a change in osmolarity. The distance between these curves or the shift is measured to determine the value of osmolarity for given solution.

Figure 8B:
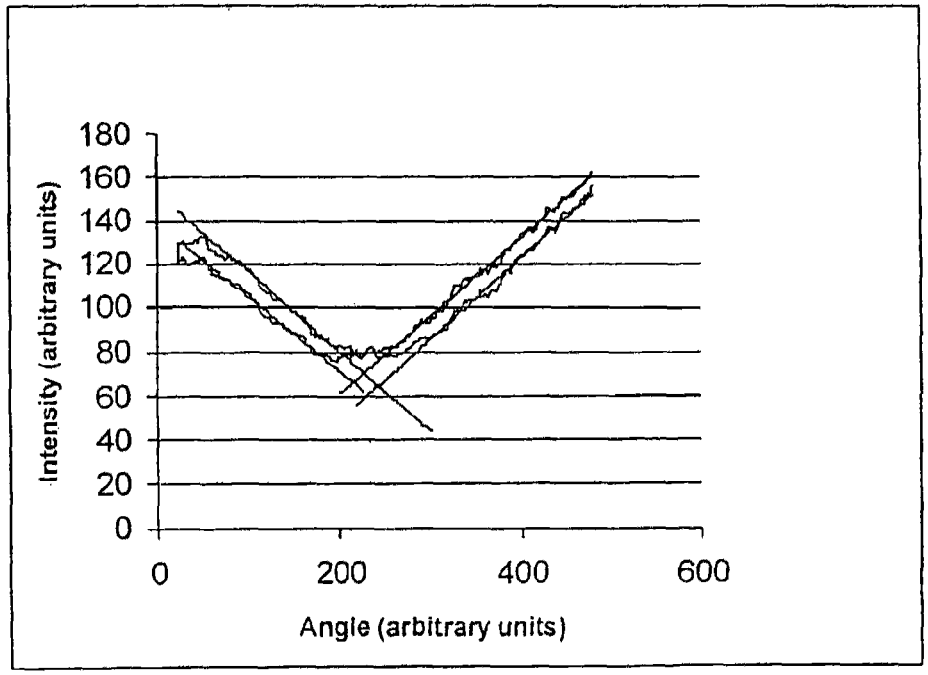
FIG. 8b is a graph showing a straight line fit method of determining the shift between the two curves.

One way to measure the shift between the curves shown in FIG. 8a, is to fit a straight line to each side of the curve. The point where these lines cross can be noted, and this performed for each curve. This will yield two distinct points separated by a distance, and this distance is representative of the shift in the actual curves. This is shown in FIG. 8b.

Figure 9A:
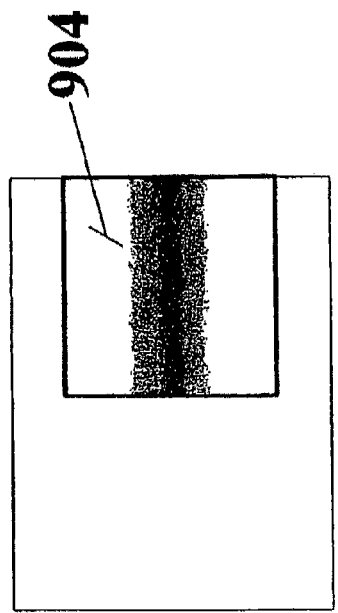
FIGS. 9a and 9b are representations of images generated using the osmometer of FIG. 4a, depicting a data acquisition step.
Figure 9B:
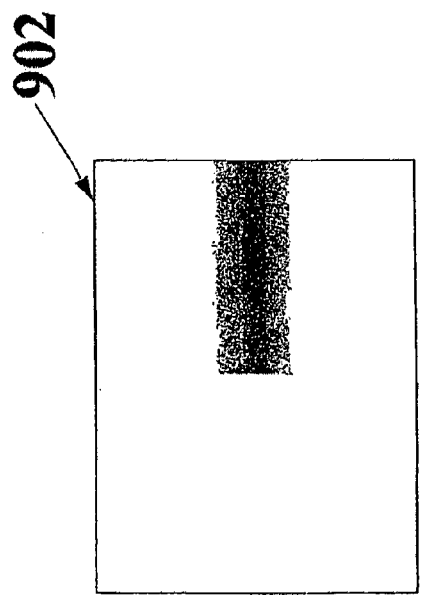
Figure 9C:
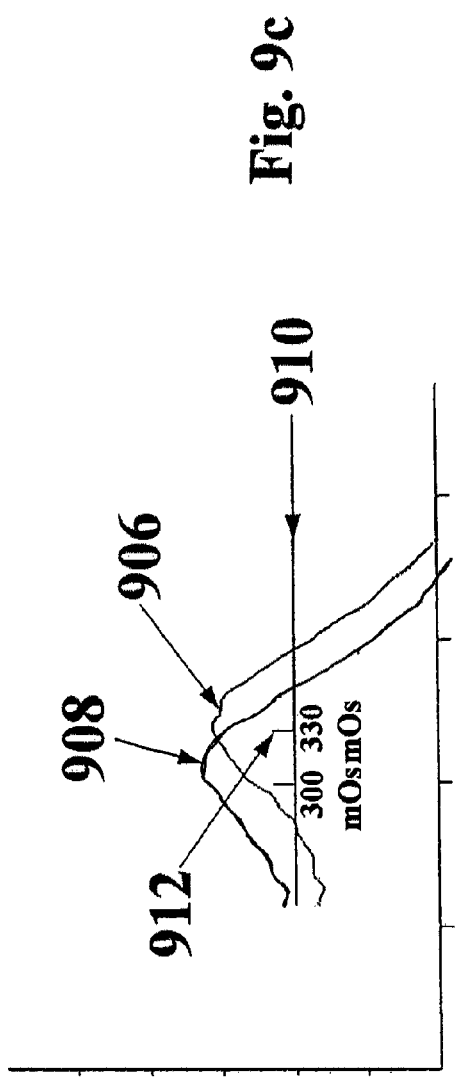
FIG. 9c is a graph depicting analysis and processing performed by a computer or microprocessor of an SPR signal to determine osmolarity of a tear.

Another method of successful detection of the vertical position of the dark line was to find the average position, plot the data and find the weighted center of the curve. It is beneficial to normalize the data first so that cut off values will not need to be determined for each solution. FIGS. 9a-9c show the process of data analysis using the centroid method. Placement of a tear sample upon the sensing surface generates an image on the CCD with a dark line covering a portion of the horizontal field amongst a bright field at some vertical position 902 (FIG. 9a). A frame of video is acquired and stored on a PC. A computer program may be written to allow the user the ability to select a region of interest 904 (FIG. 9b)in the image namely the dark line and a portion of the bright field above and below the line with a click and drag of a mouse. A button is pressed and the software begins averaging the selected region of interest selected with the mouse. The software averages the brightness of all the pixels in each horizontal row of the region to reach one brightness value for each row. The resulting data can be thought of as the region collapsed into a single vertical line, of the same height as the original region, where each point on the line is as bright or dark as the average of the whole sideways row of the original region at that height. This produces a single curve representing the average vertical position of the dark line 906 (FIG. 9c).

Adding a sample of different osmolarity causes a shift of the curve, producing two similar shaped but laterally translated SPR curves 906 and 908 (FIG. 9c). The processing continues to create a cutoff level 910 to separate the peak from the rest of the curve, and calculates the center-of-gravity or centroid of the remaining data points in the peak. This method is more robust than choosing the single apex of the curve, since it involves more data near the curve in its final result, and some curves may be oddly asymmetrical, and give inaccurate apexes. Each of the curves peak sections generated from solutions of different osmolarity are centroided and a tick mark 912 is drawn below and assigned a value on a horizontal scale, which can be calibrated to the osmolarity value of the solution.

Photodiode Method and Probe Design

Another configuration of an SPR tear osmometer involves the replacement of the CCD camera with a multi-element photodiode. Miniaturization is conceived to play a role in the success of a commercial medical device as practical reasons prevent the practicing physician from using every technological instrument that is available in their field, simply due to lack of office space. To remove the CCD camera from the system may not save substantial money from the component standpoint; it will save in post processing hardware (i.e. frame grabber, computer). The use of a CCD camera merely simplifies things for the research staff, and use of a computer allows one to make changes quickly. Computers are problematic and add expense so it is desirable from many fronts to have standalone, even portable devices.

Figure 10A:
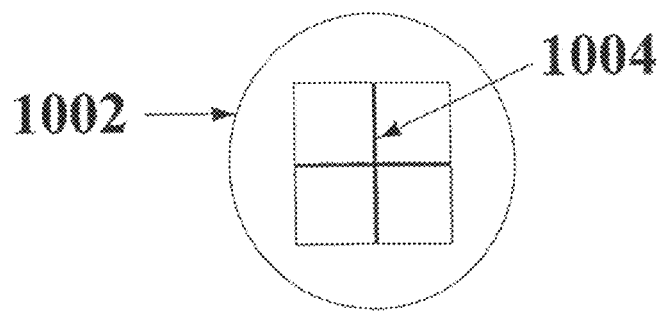
FIG. 10a is a schematic front elevational view of a quadrant photodiode detector utilizable in an osmometer in accordance with the present invention.
Figure 10B:
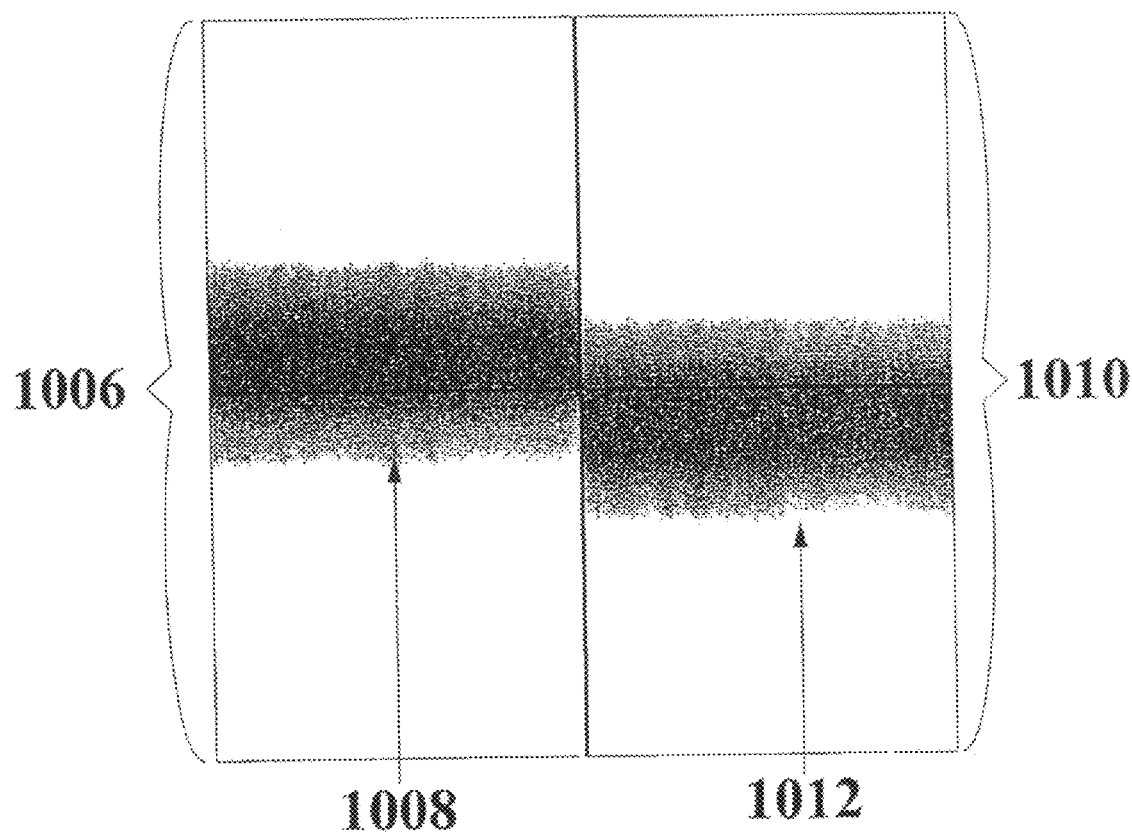
FIG. 10b is a view similar to FIG. 10a but on a larger scale, showing two SPR signals superimposed on each half of the quadrant.

An SPR tear osmometer system was built with all the same components as described above, yet with the CCD camera (FIGS. 1 and 4) being replaced with a 4-element (quadrant) photodiode (UDT Sensors, Inc. Segmented Quadrant Photodiode). Shown in FIG. 10a, a "quad detector" is essentially 4 photodiodes 1002 on the same substrate with a small deadspace 1004 in between. In this case the vertical position of the dark line is determined by allowing a portion of the dark line to be above and a portion below the upper and lower quadrants as shown in FIG. 10b. The right upper and lower quadrants 1006 might represent a sample taken from the right eye with a particular osmolarity value and vertical position of the dark line 1008, and the left upper and lower quadrants 1010 a sample from the left eye with corresponding dark line 1012. A photodiode generates a current when light is incident on the surface. The upper and lower photodiode will each generate their own current based the amount of light incident upon them which is affected by the position of the dark line. In practice the currents are amplified (Burr-Brown Corp. OPA-128 Current Op-Amp) and converted to voltages which can be compared and the relative position of the dark line (SPR minimum) be inferred. Very similar processing can be done as described with the image obtained from the CCD, however in the photodiode case one is dealing with analog voltages instead. Analog voltages can be digitized with a computer or preferable a microprocessor which can operate on the digitized voltages to produce a value corresponding to the position of the dark line and hence the osmolarity of the sample.

The use of a photodiode as the detector and integrated electronics for signal processing, micro-optics, and novel prism configurations can dramatically reduce the size of the entire system, and would make for a production instrument that could be produced in high volume relatively inexpensively. Though numerous configurations for SPR spectroscopy have been proposed for analysis of chemical and biological agents, none have been specific to tear osmolarity and the difficulties associated with nanoliter sample size, resolution, sample placement, etc.

Figure 11:
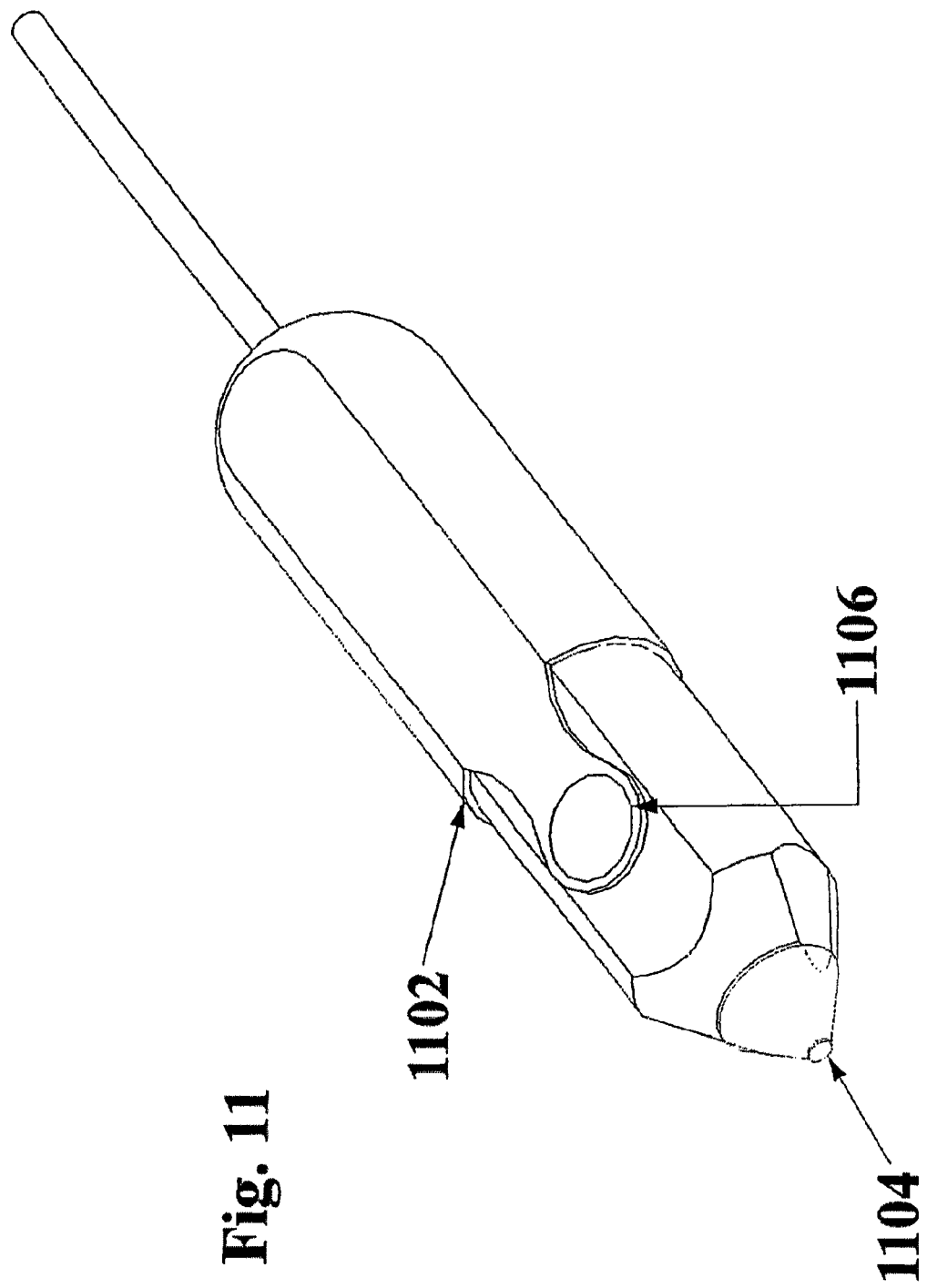
FIG. 11 is a schematic perspective view of a handheld SPR tear osmometer in the form of a hand-held probe, miniaturizing and simplifying the instrument.

The level of complexity of the optical system of an SPR spectroscope is simple enough to be miniaturized into a hand-held probe. As long as the angle of incident light is correct, SPR will occur no matter what the volume of the solution is—that is rather than probing the tear strip and capilating tear fluid into a micropipette, the sensing surface of the instrument can come in contact with the tear film itself. This cuts out a step of having to extract the tear, and solves the problems of tear placement on the sensing surface. FIG. 11 shows a computer model of a tear osmometer probe, and a handpiece 1102 of the probe includes a button 1106 that is pressed to make the measurement, contains all the necessary components of the SPR system.

Figure 12:
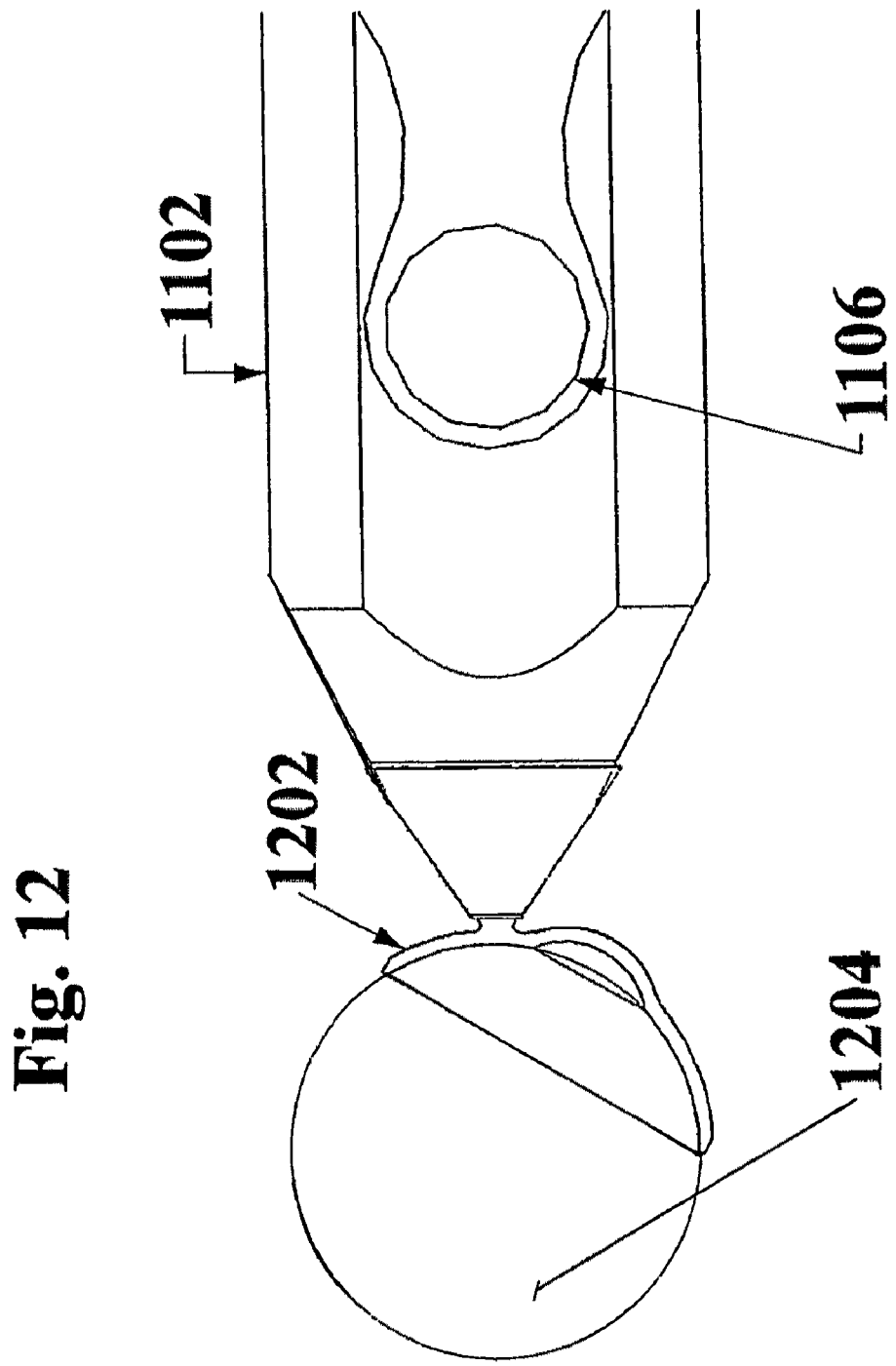
FIG. 12 is a schematic partial side elevational view of the hand-held SPR tear osmometer probe of FIG. 11, touching the tear film of the eye in the area of the sclera.
Figure 13:
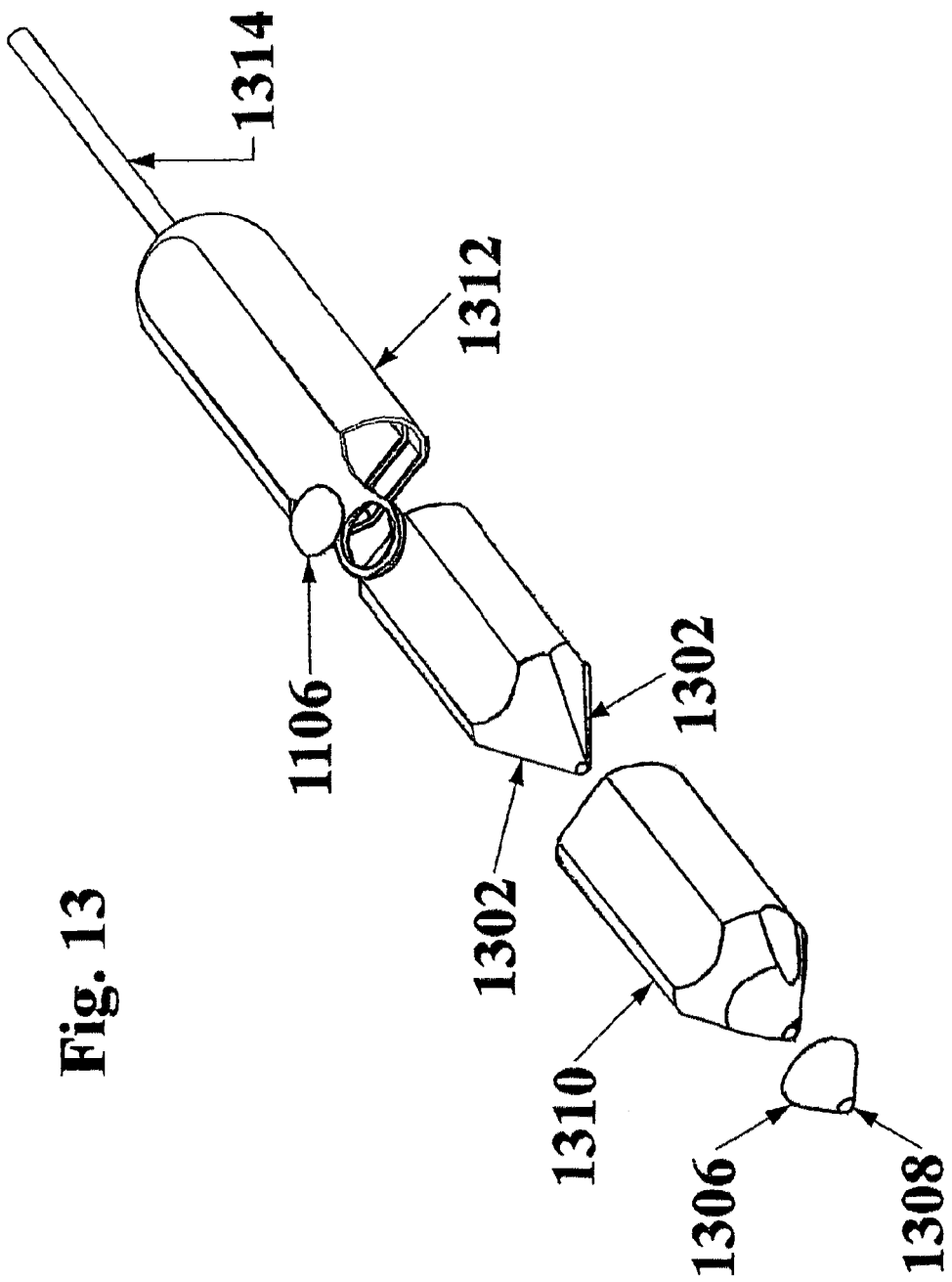
FIG. 13 is a schematic exploded view of the SPR tear osmometer probe of FIGS. 11 and 12, showing a disposable sensing surface and sheath, protective shell, optical core, and component holding back shell.

The probe has a tip 1104 that is optical glass, small in diameter, approximately 3 mm by 0.5 mm thick. This tip 1104 is where the gold is deposited on the optical glass and comes in contact with the tear film 1202 anywhere on the eye 1204 (preferably the sclera) momentarily (FIG. 12). Referring to FIG. 13, the angle of incidence necessary to measure tear osmolarity is maintained by two facets that act as first surface mirrors 1302 and are part of the core 1304 of the handpiece 1102. The core is shown to be a solid piece of optical material with flats ground and polished for the angled mirrors 1302. Since the light is in the dense (glass) medium before striking the sensing surface no prism is needed under this configuration simplifying and miniaturizing the system.

Since the metallic coating used in SPR is so thin, it is not very durable and cannot stand up to repeated wiping. Also, sensing surfaces contaminate easily and degrade the SPR curve (add noise). And since this instrument is intended to be used on the general population, it is desirable in measuring tear osmolarity to have a disposable sensing surface which this design lends itself to. This is shown as a sheath 1306 that holds the sensing surface disk 1308 and the entire system (sheath and disk) are disposed of after use.

The core of the system is housed in a mounting shell 1310 that protects the core and facilitates mounting of the sheath. The back shell 1312 contains the rest of the components for the SPR system and also houses the button 1106 to initiate measurement. Power and signal output are provided via a cable 1314 exiting the back shell and signal is processed using an external processing unit that contains a microprocessor (or a computer).

Figure 14:
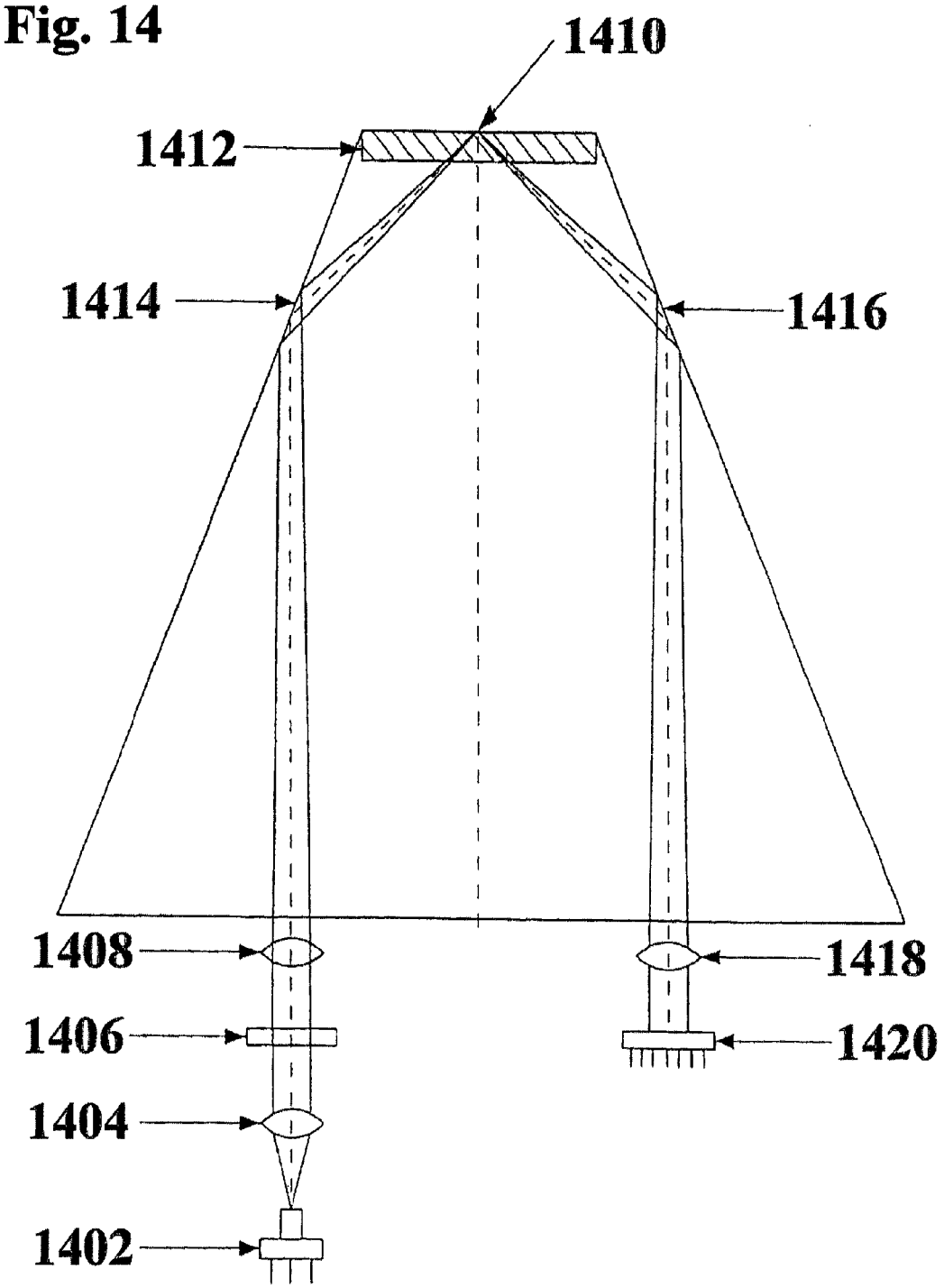
FIG. 14 shows the detailed optical schematic and ray path in and out of the optical core SPR Tear osmometer probe.

The individual optical components that are housed in the back shell are shown in FIG. 14. Light from a laser diode 1402 is collimated by a collimating lens 1404 and passes though a polarizing filter 1406. A focusing lens 1408 focuses light to a line 1410 onto a sensing surface 1412 by reflecting off an integrated mirror 1414 formed by the core surface. Light reflected from the sensing surface diverges and reflected off an integrated mirror 1416 and collimated by a collimating lens 1418. A multi-element photodiode 1420 detects the electrical SPR signal encoding a pattern of light absorption by the sensing surface. A computer or microprocessor is operated to analyze the image from the light-sensing device, i.e., photodiode.

The above-described apparatus may be modified to detect and measure a plurality of solute concentrations of a tear sample, naturally including the concentration of at least one antigenic solute or analyte in addition to salt. Gold sensing surface 108 is modified to carry attached antibodies to an antigenic analyte of interest other than a salt ion, such as a protein or other complex molecule, a bacterium, a virus, a bacterial antigen or a viral antigen. In addition, computer 426 is programmed to periodically (e.g., every 1/30 sec) process electrical signals containing image data to determine a series of absorption-line or resonance-angles and to calculate angle differences to isolate absorption line data pertaining to concentrations of solutes other than salt ions.

Thus, in addition to comparing an initial absorption-line position or resonance angle with a look-up or calibration table to determine salt concentration of a tear sample, computer 426 compares a derived absorption-line position or resonance angle with a look-up or calibration table to determine a concentration of another analyte or solute such as a protein in the tear sample. The latter table contains prerecorded data correlating absorption-line position with concentration of a particular solute or analyte. The combination of salt and other analyte concentrations facilitates disease diagnosis or potential disease conditions that may be purely ocular or affecting the entire body (diabetes, etc.).

Computer 426 may have stored in memory a number of tables of resonance angle data, each table pertaining to a respective solute that may be found in various tear samples. Each table includes resonance angle tabulations as a function of solute concentration. Accordingly, a single SPR tear osmometer may measure multiple solute concentrations by using a series of sensor surfaces 108 having different attached antibodies.

The photodiode 1001 or 1420 of the SPR apparatus is operated to transmit to computer 426 multiple electrical signals per second, wherein each of the electrical signals encodes a pattern of light absorption by antibody-carrying sensing surface 108, the electrical signals being separated from each other by at least one predetermined time interval. In addition, computer or microprocessor 426 is operated to analyze the pattern of light absorption encoded in each of the electrical signals.

When measuring tear osmolarity with the SPR device, one analyzes the portion of the SPR signal obtained within the first few milliseconds. For a given sample of tear fluid, which contains both salt solution and proteins, the salt solution comprises small molecules or ions that migrate quickly to the sensing surface. The proteins, being more bulky, take more time to reach and bind to the sensing surface. By making a two-part time-based measurement, one measures both a first signal that reflects the concentration of salt (osmolarity) and a second, larger signal that reflects both salt and protein concentration as the protein binds with the sensing surface. One determines the concentration of protein through simple signal subtraction and analysis (i.e., larger signal less smaller signal is proportional to protein concentration).

Computer 426 is programmed to analyze the patterns of light absorption to determine, for instance, angles of maximum absorption by the sensing surface (absorption-line positions). Thus, the operating of the surface plasmon resonance apparatus may more specifically include operating computer 426 to determine a surface resonance angle or absorption-line position from each of the electrical signals. These resonance angles or absorption-line positions include a first resonance angle or absorption-line position associated with a temporally first one of the electrical signals (e.g., within 1/30 second after contact of the tear sample with sensing surface 108) and a second resonance angle or absorption-line position associated with a later one of the electrical signals (e.g., at 2/30, 3/30, 4/30 second after contact of the tear sample with sensing surface 108). Computer 426 then compares the first resonance angle or absorption-line position to entries in a first calibration table to determine a first solute concentration value (osmolarity), subtracts the first resonance angle or absorption-line position and the second resonance angle or absorption-line position from one another to determine a resultant resonance angle or absorption-line position, and compares the resultant resonance angle to entries in a second calibration table to determine a second solute (e.g., protein or antigen) concentration.

The first solute concentration is a salt concentration. This is because salt migrates more quickly to the sensing surface than the other solute components of a tear sample. Concomitantly, to obtain an absorption-line position or sensing-surface resonance angle that corresponds only to the salt concentration of the tear sample, it is necessary to obtain a measurement before any substantial quantity of the other solute (e.g., proteins, bacterial antigens) has sufficient opportunity to migrate to the sensing surface. In that situation, the shift of the absorption-line or sensing surface resonance angle relative to a base position (refraction angle determined by the solvent, water, and not by any solute) is due to the salt concentration of the tear sample alone and not to any other solute concentration. A delay of no more than about 1/30 second from the time of deposition of the tear sample on the sensing surface is generally sufficiently quick so that the initial video signal captures the salt concentration with little or no error due to concentrations of other substances. Where the measurement probe contacts an eye surface to obtain a tear sample, this first signal, as well as several subsequent measurements, are inevitably made while the probe is still in contact with the eye.

Chemical Antigens for Disease Detection

The general technique for utilization of SPR as a chemical antigen sensor is as follows. It is first necessary to identify an antibody that will specifically bind to the desired chemical antigen.

Once identified, the specific antibody is bound to the sensing surface through wet chemistry techniques. Binding of antibodies to SPR sensing surfaces is well known and although various methodologies exist, one method is described below.

A tear sample is introduced on sensing surface 108 carrying the bound antibodies and if the tear sample contains the desired chemical antigen, a change in the SPR signal (change in angle where the phenomenon occurs) is observed. If no chemical antigen is in the tear sample, the signal is undisturbed. Below is a summary of the binding of the antibody and the detection of the chemical antigen.

Immobilization of the antibody

Figure 17:
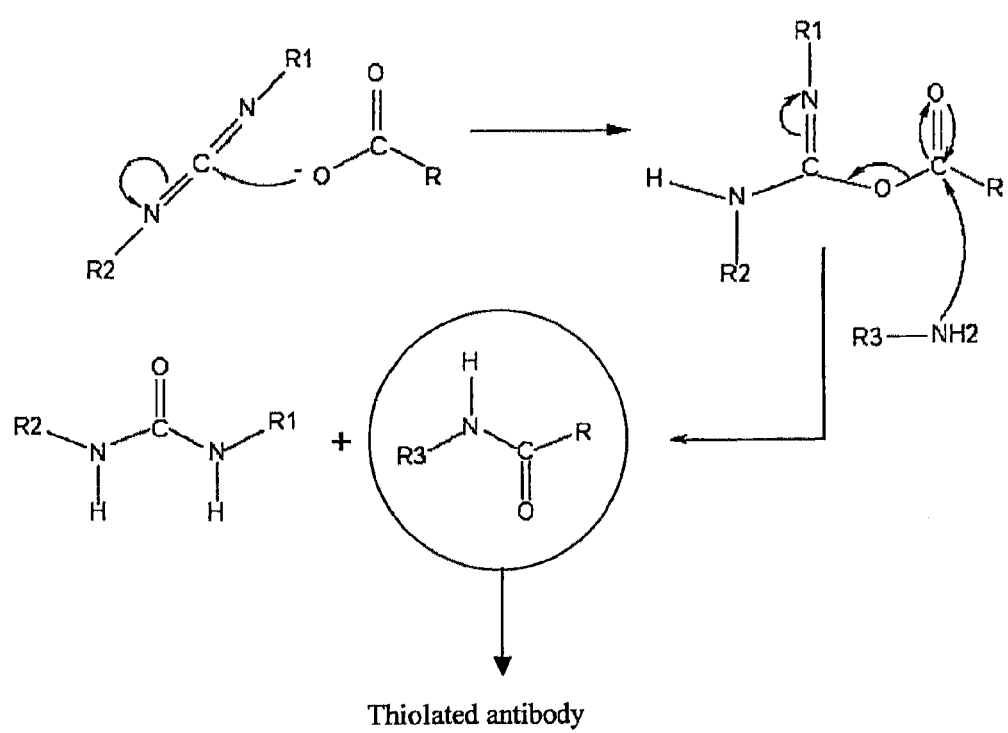
FIG. 17 is a diagram of a scheme to thiolate the antibody of FIG. 16.

The antibody can be bound to the gold sensing surface 108 using well-known thiol chemistry techniques. The thiol molecule acts as an adhesive layer, between the antibody and gold. The thiol unit chemisorps and attaches itself to gold while the other end, which has an amino group or carboxylic acid group, reacts with one of the terminal carboxylic acid or amino groups respectively, thereby attaching the antibody. Examples of the thiol adhesive could be 11-thioundecanoic acid or 2-aminoethanethiol hydrochloride. FIGS. 16 and 17 show a scheme using the latter. However, either one is equally effective and their use will be governed by the availability of the terminal reactive site on the specific antibody in question.

An SPR sensing surface 108 is produced as previously described above by depositing a 50 nm thick layer of gold onto glass with the appropriate underlayer (i.e. 2 nm chrome) for good adhesion of the gold. Prior to antibody binding, 2-aminoethanethiol hydrochloride solution is first flowed over the gold sensor surface using a flow cell with an input port, a holding chamber, an output port, and a pump as described hereinabove. The flow cell system allows for various fluids to conveniently come in contact with the sensing surface. Passing the 2-aminoethanethiol hydrochloride solution over the sensing surface results in the formation of a self-assembled monolayer (SAM). Subsequently, a mixture of the antibody and EDC is flowed over this SAM using the same flow cell apparatus. The amino groups on the SAM will react with the terminal carboxylic acid group in the antibody, resulting in the attachment of the antibody to the gold surface. The reaction mechanism is shown in FIG. 17. FIG. 16 shows the chemical structure of the different chemical components that are involved in the reaction. In the Figures, R1, R2, and R3 are shorthand representations of the regions of the molecule not taking part in the reaction. It is common practice to use this shorthand in describing reaction mechanisms on paper.

After this process, the sensing surface 108 carries a specific immobilized antibody and is ready for chemical antigen detection. The sensing surface 108 is then installed in the instrument (for example, sensing surface 1104 and 1308 is installed on the tip of the glass core 1310 in the probe design shown in FIGS. 11 and 13) and is then be brought in contact with a tear sample. Depending on the antibody present, preferential binding will occur specific to the respective antigen thereby leading to an SPR signal.

Now, more detail is provided the specific pathologies that can be detected, monitored and/or staged by creating antibodies for specific chemical antigens that can be bound to the gold sensing surface.

Inflammation in Tears

Detection and monitoring of inflammation in the tears is helpful in diagnosing and staging blepharitis, dry eye and ocular allergy.

Antibodies to pro-inflammatory cytokines and chemokines including, but not limited to, Tumor necrosis factor-alpha, Interleukin 1-beta (IL-1-beta), IL-11, IL-4, IL-4, IL-6, interleukin-6 soluble receptor (IL-6sR), IL-7, eotaxin-2, macrophage inflammatory protein 1alpha (MIP-1alpha), MIP-1beta, monokine induced by interferon (MIG)-gamma, and interferon-gamma-inducible protein (IP)-10 can be used to measure these cytokines and chemokines with SPR.

Mucus

In dry eye there is a loss of specific mucins from the eye surface. For example, in dry eye there is a decrease in MUC 5a.

Antibodies to MUC 1, 4, 5a, 16 can be used to measure these mucins with SPR technology.

Allergic Eye Disease

Allergic conjunctivitis is a type I hypersensitivity reaction that begins when an allergen, such as pollen, stimulates the synthesis of allergen-specific IgE antibodies. IgA antibodies are increased in vernal allergic eye disease. Antibodies can be raised to IgE and IgA and these antibodies can be measured using SPR technology.

Bacterial Infections

Bacterial infections can be diagnosed and categorized using the SPR tear probe, permitting, for example, the differentiation between gram negative and gram positive infections.

For example, an antibody to specific gram-negative bacterial lipopolysaccharide (LPS) O antigens can be used with SPR technology to identify gram negative infections. Antibodies can also be created to recognize individual species of bacteria such as, but not limited to, *Pseudomonas, Proteus mirabilis* and *Staphylococcus aureus*.

Viral Infections

It can be difficult to diagnosis and differentiate herpes simplex and herpes zoster. Specific antibodies can be created to these and other viruses for diagnostic purposes that can be used with SPR technology.

Fungal Infections

It is difficult to diagnose fungal infections. Antibodies have been created for specific fungal organisms such as, but not limited to *Aspergillus, Blastomyces Coccidioides* and *Histoplasma*.

*Chlamydial* and *Acanthameobal* Infections

Antibodies can be raised against *Chlamydia* and *Acanthameoba* to diagnosis these infections in the tear film using SPR technology.

Practical Device Operation

For protein detection in tear fluid, none of the hardware of the device described above with references to FIGS. 1-15 requires modification. Proteins will migrate to the gold sensing surface and attach thereto, so as to permit concentration detection via SPR techniques. To detect proteins, the software must be modified as discussed above. In the case of measuring concentrations of chemical antigens (other than proteins) for disease detection, the hardware also needs no modification except that the sensing surface 108 is modified to carry attached antibodies. Again, computer 426 is modified to include additional programming as described above. Gold sensing surface 108 is modified to carry attached antibodies to an antigenic analyte of interest, such as a complex molecule, a bacterium, or a virus. In addition, computer 426 is programmed to periodically (e.g., every $\frac{1}{30}$ sec) process electrical signals containing image data to determine a series of absorption-line or resonance-angles and to calculate angle differences to isolate absorption line data pertaining to concentrations of solutes other than salt ions.

In the detection of proteins and antigenic analytes, the software (or signal detection electronics—i.e., microprocessor) captures the signal generated over a period of time. For instance, when the sensing surface is brought into contact with the tear sample, the signal is captured at the instant the sensing surface comes in contact with the sample. Then a signal is captured every $1/30^{th}$ of a second thereafter, as for example in a standard video camera, for several seconds. The first frame of video represents the signal related to tear osmolarity. As the proteins begin to bind with the sensing surface or as the antigenic analyte begins to bind to the antibodies on the sensing surface, the signal will change, and the software will analyze the successive frames obtained thereafter to determine protein or other antigenic analyte concentration. For each specific chemical antigen to be identified, a sensing surface is provided with the required antibody bound to the surface fir signal detection.

In the probe instrument described herein with reference to FIGS. 11-13, the small sensing surface tip has bound to it the specific antibody. The balance of the hardware described with reference to FIGS. 1-15 does not change from the described configuration. Since the host material is still human tears, the nominal angular range at which SPR occurs does not change hence no adjustment is needed to the incident angle of the laser beam. The signal detection still occurs using a multi-element detector.

Again, the software requires some modification. Since with osmolarity or salt concentration measurements, the software analyzes the acquired SPR signal. For a given osmolarity, the angle of the SPR signal is determined and this value is compared to the calibration table stored in the computer.

When detecting chemical antigens using specific antibodies bound to the sensing surface, the software must be "aware" that a measurement other than osmolarity was to take place. As a commercial device, a user purchases the antibody specific sensing surface tip, applies it to the instrument, and brings the tear sample in contact with the sensing surface. If the chemical antigen is present, the SPR signal shows a change and the software analyzes the SPR signal to determine the degree of change.

Although the invention has been described in terms of particular embodiments and applications, one of ordinary skill in the art, in light of this teaching, can generate additional embodiments and modifications without departing from the spirit of or exceeding the scope of the claimed invention. For instance, it is to be understood that the present invention is capable of determining concentrations of some solutes in tear samples, in addition to salt ions, by using a gold sensing surface that has no antibodies. Some proteins, for instance, naturally migrate to the gold sensing surface and result in a modified resonance angle as discussed hereinabove. Accordingly, it is to be understood that the drawings and descriptions herein are proffered by way of example to facilitate comprehension of the invention and should not be construed to limit the scope thereof.

What is claimed is:

1. A medical diagnostic method comprising:
providing a surface plasmon resonance apparatus;
providing said surface plasmon resonance apparatus with a sensing surface;
moving at least a portion of the surface plasmon resonance apparatus to bring said sensing surface into direct contact with a tear film or tear-bearing portion of a patient's eye; and
operating the surface plasmon resonance apparatus to determine concentration of a solute in the tear film or tear-bearing portion of the patient's eye, the operating of the surface plasmon resonance apparatus including binding said solute to said sensing surface during the direct contact of said sensing surface with the tear film or tear-bearing portion of the patient's eye.

2. The method defined in claim 1 wherein the surface plasmon resonance apparatus includes a light-sensing device and a computer or microprocessor operatively linked to said light-sensing device, the operating of the surface plasmon resonance apparatus including:
operating said light-sensing device to transmit to said computer an electrical signal encoding a pattern of light absorption by said sensing surface; and
operating said computer or microprocessor to analyze the pattern of light absorption encoded in said electrical signal.

3. The method defined in claim 2 wherein the operating of the surface plasmon resonance apparatus includes:
operating said light-sensing device to transmit to said computer multiple electrical signals per second, each of said electrical signals encoding a pattern of light absorption by said sensing surface, said electrical signals being separated from each other by at least one predetermined time interval; and
operating said computer or microprocessor to analyze the pattern of light absorption encoded in each of said electrical signals.

4. The method defined in claim 3 wherein the operating of the surface plasmon resonance apparatus further includes operating said computer or microprocessor to determine a surface plasmon resonance angle or absorption-line position from each of said electrical signals, the resonance angles or absorption-line positions including a first resonance angle or absorption-line position associated with a temporally first one of said electrical signals and a second resonance angle or absorption-line position associated with a later one of said electrical signals.

5. The method defined in claim 4 wherein the operating of the surface plasmon resonance apparatus further includes operating said computer or microprocessor to compare said first resonance angle or absorption-line position to entries in a first calibration table to determine a first solute concentration value; to subtract said first resonance angle or absorption-line position and said second resonance angle or absorption-line position from one another to determine a resultant resonance angle or absorption-line position; and to compare said resultant resonance angle to entries in a second calibration table to determine a second solute concentration.

6. The method defined in claim 2 wherein said light-sensing device is a camera and said electrical signal is a video signal.

7. The method defined in claim 2 wherein said light sensing device is a multi-element photodiode and said electrical signal is an analog difference signal.

8. The method defined in claim 2 wherein the operating of said computer or microprocessor includes operating said computer or microprocessor to compare an absorption-line position with prerecorded data correlating absorption-line position with osmolarity.

9. The method defined in claim 1 wherein said surface plasmon resonance apparatus takes the form of a portable probe, the moving of said portion of said surface plasmon resonance apparatus comprising manipulating the probe to bring said sensing surface directly into contact with said tear film or tear-bearing portion of the patient's eye.

10. The method defined in claim 9 wherein providing said surface plasmon resonance apparatus with said sensing surface comprises disposing a metallic film carrying sheath in a predetermined position on an operative tip of the probe.

11. The method defined in claim 1 wherein providing said surface plasmon resonance apparatus with the sensing surface comprises disposing a metallic film carrier in a predetermined position on the surface plasmon resonance apparatus.

12. The method defined in claim 11 wherein the metallic film carrier is a plate, the disposing of the metallic film carrier including placing said plate onto a cylindrical prism of said surface plasmon resonance apparatus.

13. The method defined in claim 1, further comprising operating said surface plasmon resonance apparatus to determine concentrations of at least two different solutes in said tear film or tear-bearing portion of the patient's eye.

14. The method defined in claim 13 wherein the operating of said surface plasmon resonance apparatus includes determining a plurality of resonance angles or absorption-line positions each associated with a respective point in time and subtracting one resonance angle from another to determine a resultant angle, further comprising determining the concentration of one of said solutes corresponding to said resultant angle.

15. The method defined in claim 1 wherein the binding of said solute to said sensing surface includes providing said sensing surface with binding molecules or ligands.

16. The method defined in claim 15 wherein the binding of said solute to said sensing surface includes forming bonds between said solute and said binding molecules or ligands on said sensing surface.

17. A medical diagnostic system comprising a surface plasmon resonance apparatus having a sensing surface for contacting a tear sample and configured to interact with a plurality of different solutes and further having a light-sensing device and a computer or microprocessor operatively linked to said light-sensing device for receiving therefrom a plurality of electrical signals encoding patterns of light absorption by said sensing surface, said computer or microprocessor being programmed to analyze data from said light-sensing device to determine concentrations of the plurality of different solutes in a single contiguous or unitary tear sample in contact with said sensing surface by analyzing the patterns.

18. The system defined in claim 17 wherein said light-sensing device is a camera and said electrical signal is a video signal.

19. The system defined in claim 17 wherein said light sensing device is a multi-element photodiode and said electrical signal is an analog difference signal.

20. The system defined in claim 17 wherein said computer or microprocessor is programmed to compare an absorption-line position with prerecorded data correlating absorption-line position with solute concentration.

21. The system defined in claim 17 wherein said tear sample is a film or tear-bearing portion of a patient's eye.

22. A medical diagnostic system comprising a surface plasmon resonance apparatus having a sensing surface for directly contacting a tear-bearing portion or tear film of an eye of a patient and further having a light-sensing device and a computer or microprocessor operatively linked to said light-sensing device for receiving therefrom an electrical signal encoding a pattern of light absorption by said sensing surface, said computer or microprocessor being programmed to analyze data from said light-sensing device to determine a solute concentration parameter of the tear-bearing portion or tear film in contact with said sensing surface, said surface plasmon resonance apparatus including a handheld portable casing with an operative tip adapted to facilitate direct contact of said sensing surface on said operative tip with said tear-bearing portion or tear film of the patient's eye.

23. A medical diagnostic system comprising a surface plasmon resonance apparatus having a sensing surface for contacting a tear film or tear-bearing portion of a patient's eye and further having a light-sensing device and a computer or microprocessor operatively linked to said light-sensing device for receiving therefrom an electrical signal encoding a pattern of light absorption by said sensing surface, said computer or microprocessor being programmed to analyze data from said light-sensing device to determine a solute concentration parameter of the tear film or tear-bearing portion of the patient's eye in contact with said sensing surface, said sensing surface including a first layer of a first metal disposed on a second layer of a second metal.

24. The system defined in claim 23 wherein said second layer is in turn disposed on a substrate of transparent material.

25. The system defined in claim 23 wherein said sensing surface is provided with binding molecules or ligands.

26. The method defined in claim 25 wherein said binding molecules or ligands are selected for forming bonds with at least one predetermined solute.

27. A medical diagnostic method comprising:
providing a surface plasmon resonance apparatus;
providing said surface plasmon resonance apparatus with a disposable sensing surface, said sensing surface being adapted for placement in direct contact with a tear-bearing portion or tear film of an eye;
after providing said surface plasmon resonance apparatus with said sensing surface, moving at least a portion of the surface plasmon resonance apparatus to bring said sensing surface into direct contact with a tear film or tear-bearing portion of the eye;
operating the surface plasmon resonance apparatus to determine a solute concentration in the tear tear film or tear-bearing portion; and
after operating said surface plasmon resonance apparatus to determine a solute concentration in the tear film or tear-bearing portion, removing said sensing surface from said surface plasmon resonance apparatus.

28. The medical diagnostic method defined in claim 27, further comprising, after removing said sensing surface from said surface plasmon resonance apparatus, providing said surface plasmon resonance apparatus with another sensing surface.

29. The medical diagnostic method defined in claim 27 wherein providing said surface plasmon resonance apparatus with said disposable sensing surface comprises removably disposing a metallic film carrier in a predetermined position on the surface plasmon resonance apparatus.

30. A medical diagnostic method comprising:
providing a surface plasmon resonance apparatus;
providing said surface plasmon resonance apparatus with a sensing surface configured to interact with at least two different solutes;
placing said sensing surface into contact with a single contiguous or unitary tear sample; and
operating the surface plasmon resonance apparatus to determine concentrations of the at least two different solutes in the single contiguous or unitary tear sample while the sensing surface is in contact with same based on a plurality of signals detected by the sensing surface.

31. The method defined in claim 30 wherein the operating of said surface plasmon resonance apparatus includes detecting a first reflection minimum occurring at a first point in time and corresponding to a first one of said different solutes and subsequently detecting a second reflection minimum occurring at a second point in time later than said first point in time and corresponding to a second one of said different solutes.

32. The method defined in claim 31 wherein the operating of said surface plasmon resonance apparatus further includes:

measuring a first resonance angle or absorption-line position associated with said first reflection minimum;

measuring a second resonance angle or absorption-line position associated with said second reflection minimum;

subtracting said first resonance angle from said second resonance angle to determine a resultant angle; and determining the concentration of said second one of said different solutes from said resultant angle.

33. The method defined in claim 32 wherein the determining of the concentration of said one of said solutes includes operating said surface plasmon resonance apparatus to compare said resultant angle to entries in a calibration table.

34. The method defined in claim 30 wherein the operating of said surface plasmon resonance apparatus includes determining a plurality of resonance angles or absorption-line positions each associated with a respective point in time and subtracting one resonance angle from another to determine a resultant angle, further comprising determining the concentration of one of said solutes corresponding to said resultant angle.

35. The method defined in claim 30 wherein said tear sample is a film or tear-bearing portion of the patient's eye, the placing of said sensing surface into contact with said single contiguous or unitary tear sample comprising moving at least a portion of the surface plasmon resonance apparatus to bring said sensing surface into direct contact with said tear film or tear-bearing portion of the patient's eye.

* * * * *